United States Patent
Kumar et al.

(10) Patent No.: US 9,688,996 B2
(45) Date of Patent: *Jun. 27, 2017

(54) USE OF A MAIZE UNTRANSLATED REGION FOR TRANSGENE EXPRESSION IN PLANTS

(71) Applicants: DOW AGROSCIENCES LLC, Indianapolis, IN (US); Sandeep Kumar, Carmel, IN (US); Manju Gupta, Carmel, IN (US); Diaa Alabed, Carmel, IN (US)

(72) Inventors: Sandeep Kumar, Indianapolis, IN (US); Manju Gupta, Indianapolis, IN (US); Diaa Alabed, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 130 days.

This patent is subject to a terminal disclaimer.

(21) Appl. No.: 14/416,811

(22) PCT Filed: Aug. 8, 2013

(86) PCT No.: PCT/US2013/054102
§ 371 (c)(1),
(2) Date: Jan. 23, 2015

(87) PCT Pub. No.: WO2014/028295
PCT Pub. Date: Feb. 20, 2014

(65) Prior Publication Data
US 2015/0203856 A1    Jul. 23, 2015

Related U.S. Application Data

(60) Provisional application No. 61/684,255, filed on Aug. 17, 2012.

(51) Int. Cl.
*C12N 15/82*    (2006.01)

(52) U.S. Cl.
CPC ..... *C12N 15/8216* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 2004/0158887 A1* | 8/2004 | Cowen | C12N 15/8216 800/278 |
| 2005/0102713 A1* | 5/2005 | Merlo | C12N 15/8216 800/278 |
| 2015/0337302 A1* | 11/2015 | Donohue | A01N 63/02 514/44 A |

OTHER PUBLICATIONS

Hunt, Front Plant Sci 2:109 (2012).*
Wright et al., Proc Natl Acad Sci 107(47):20240-45 (2010).*

* cited by examiner

*Primary Examiner* — Cathy Kingdon Worley
*Assistant Examiner* — Russell Boggs
(74) *Attorney, Agent, or Firm* — Yung H. Lee

(57) ABSTRACT

Provided are methods, vectors and gene constructs for enhancing expression of a recombinant nucleic acid sequence in transgenic plants and plant tissues. According to the present invention, nucleic acid sequences are obtained and/or derived from the 3' untranslated regions of genes encoding ubiquitin proteins and engineered to flank respective portions of a selected coding region of a vector. The vector construct may be introduced into plants and/or plant tissues through conventional or gene targeting procedures, resulting in enhanced expression of the selected coding region. In some embodiments, the selected coding region is a chimeric gene or gene fragment expressing one or more proteins known to impart a level of insecticidal activity to a transgenic plant and/or plant tissue.

18 Claims, 13 Drawing Sheets

SEQ ID NO: 1 gtcatgggtcgtttaagctgccgatgtgcctgcgtcgtctggtgccctctctc
catatggaggttgtcaaagtatctgctgttcgtgtcatgagtcgtgtcagtgt
tggtttaataatggaccggttgtgttgtgtgtgcgtactacccagaactatga
caaatcatgaataagtttgatgtttgaattaaagcctgtgctcattatgttc
tgtctttcagttgtctcctaatatttgcctgcaggtactggctatctaccgtt
tcttacttaggaggtgtttgaatgcactaaaactaatagttagtggctaaaat
tagttaaaacatccaaacaccatagctaatagttgaactattagctattttg
gaaaattagttaatagtgaggtagttatttgttagctagctaattcaactaac
aattttagccaactaacaattagtttcagtgcattcaaacaccccttaatg
ttaacgtggttctatctaccgtctcctaatatatggttgattgttcggtttgt
tgctatgctattgggttctgattgctgctagttcttgctgaatccagaagttc
tcgtagtatagctcagattcatattatttatttgagtgataagtgatccaggt
tattactatgttagctaggttttttttacaaggataaattatctgtgatcata
attcttatgaaagctttatgtttcctggaggcagtggcatgcaatgcatgaca
gcaacttgatcaccagctgaggtagatacggtaacaaggttcttaaatctg
ttcaccaaatcattggagaacacacatacacattcttgccagtcttggttaga
gaaatttcatgacaaaatgccaaagctgtcttgactcttacttttggccatg
agtcgtgac

FIG. 1A

SEQ ID NO: 2 ZMEXP9396.1 agttctagcagcttgcctgcatgttccgctgtcactgcctcactaggcacgtt
cacaataccatcgatggcttgcctgcctctatagaatgctgatctactcttca
ctggaggccccttatatataggacaaaaatcccaatttgtttggaaaacca
caagtagggatatatctgtcgaattctcgtatgcaacggcaacgccgttctac
ccctcaacttttttttttcctttttctactttgcaacatgcaacaagggctgt
cattgatcgaaattcaaatatatgttcattgggaattccatgcgactgccta
aactctaggaagtttcacttgtcctgtttcatatgtatgtatgcattgtagcc
ttgttgtatttcctcaatgtcttggttgctttcatcggttagagttcttgacg
actgttgcagagattctgtcggagtatattcagggtcgcctattaccagacat
gctgcccggacaacatgttgattcgttcattggcagcgcaacatgcaattaga
aattaacagctactctagaacaagcaaataacagctgtcgctaaaattcaata
ttccatccctgttaacattgaatttattgtcttgtttatgaaccctatgtatc
tgacagcaccattgccttttttttacttaggcggtccattattgtcacacccg
gatttaaagagaaagttggatgcatcttatacatgcgacaaagaagaaaacat
atatatgtatagagataaatgtcataataacatcaaaatacttattacaatgc
gtaagtcttacaaaataaaagataaatataaatcaaactaaaatctatctttg
gcgccaataagtcaactgggagatgccacctagatcagatcaaattcctcgtt
gtgtggctcctcttgaaccatctgttcttcctgtggggagtgtgagacagc
aagggtgagctcacacatgttcattgttcaacaagttgtggggaataggagtt
catgcgatttgtaaggctaatcaacaatag

FIG. 1B

SEQ ID NO: 3 ZMEXP9707.1

Gctcagcttctccatttgcatggtctagtagcttgctttgtactgctagcgcc
ggtcgatccgtcgcaatcgtcatggatcatctctatcttgttgttgcgctg
ttcataatttggtatatttgccattccgctattgtgtactctttggcatacat
acaataattaaaatggcgttgcgtggctctcatataattaaccttcacataac
ctgaagactcaagtacgtatagtatgggcaactttattgtagatactatctgg
agtctcgaatatttgtcgtccgctagttcatatttaaactaaacaacgataaa
taaaaaagaactaagtgagtatattttttgtgggagaagggttatccattaa
tacatccacggttctgtaaattccatttcatgacatgaaaaaggaaaaacgc
atccaatagcccattatgtaaatatgtctaccgtctatccattggacaagtta
tatattaatgactagtttggtaacctcatttttttaaggattttcgtttttta
agcgaaattagttcattttaccttggcaaatagaatttttagaaaaaaatg
gtgttctcaaactagccttaaattttttagaaatgagaatattattaatatt
ccatcttccaggggcggatttgggcctcgggccacctgggccgtggcccaggg
cgcagcccaaaaaccctcttatataggtcttttttcaaccaaaaaatctag
accaaaatacatttcagcctaaaagatctcctgctgcaccgattgagtctggt
ggcgctggcggcctccctcagtcgctcaagccacgagaacacactctttcaat
tatttcgcaaacatgcgcagctgcgtttcctatgttgccagcggcgcggccgc
ctccattcagtcctctatcgctctccacgccttcaggctctacgaatccgata
agggaacaaggcagcaacctctaaggcagccgggcgggctctgactcaggcat
ccgccaccgccagtccgcctccaacgtcctgcgaacctgtagcaatgacgcg
t

FIG. 1C

USE OF A MAIZE UNTRANSLATED REGION FOR TRANSGENE EXPRESSION IN PLANTS

CROSS-REFERENCE TO RELATED APPLICATIONS

This application claims priority under 35 U.S.C. §119 of U.S. provisional patent application Ser. No. 61/684,255 filed Aug. 17, 2012, which application is hereby incorporated by reference in its entirety. This application is a national phase entry of international application PCT/US2013/054102 filed Aug. 8, 2013, which application is hereby incorporated by reference in its entirety.

FIELD OF THE INVENTION

This invention is generally related to the field of genetic engineering, and more specifically the field of transgene expression in plants.

BACKGROUND OF THE INVENTION

Recombinant DNA technology and genetic engineering have made it routinely possible to introduce desired DNA sequences into plant cells to allow for the expression of proteins of interest. For commercially viable transformation events, however, obtaining desired levels of stable and predictable expression in important crops remains challenging.

One method of expressing heterologous genes at desired levels in crops involves manipulation of the regulatory mechanisms governing expression in plants. The regulation may be transcriptional or post-transcriptional and can include, for example, mechanisms to enhance, limit, or prevent transcription of the DNA, as well as mechanisms that limit or increase the life span of an mRNA after it is produced. The DNA sequences involved in these regulatory processes can be located upstream, downstream or even internally to the structural DNA sequences encoding the protein product of a gene.

To regulate transcription in a transgenic plant, various types of promoters may be employed. Promoters can be used to control the expression of foreign genes in transgenic plants in a manner similar to the expression pattern of the gene from which the promoter was originally derived. In general, promoters are classified in two categories: "Constitutive" promoters express in most tissues most of the time, while "regulated" promoters are typically expressed in only certain tissue types (tissue specific promoters) or at certain times during development (temporal promoters). Expression from a constitutive promoter is typically more or less at a steady state level throughout development. Genes encoding proteins with house-keeping functions are often driven by constitutive promoters. Examples of constitutively expressed genes in maize include actin and ubiquitin (Ubi).

Further improvements in transcription can be obtained in transgenic plants by placing "enhancer" sequences upstream (5') of the promoter. Enhancer elements are cis-acting and increase the level of transcription of an adjacent gene from its promoter in a fashion that is relatively independent of the upstream position and orientation of the enhancer. Such sequences have been isolated from a variety of sources, including viruses, bacteria and plant genes. One example of a well characterized enhancer sequence is the octopine synthase (ocs) enhancer from the *Agrobacterium tumefaciens*, as described in U.S. Pat. Nos. 5,837,849, 5,710,267 and 5,573,932. This short (40 bp) sequence has been shown to increase gene expression in both dicots and monocots, including maize, by significant levels. Tandem repeats of this enhancer have been shown to increase expression of the GUS gene eight-fold in maize. It remains unclear how these enhancer sequences function. Presumably enhancers bind activator proteins and thereby facilitate the binding of RNA polymerase II to the TATA box. WO95/14098 describes testing of various multiple combinations of the ocs enhancer and the mas (mannopine synthase) enhancer which resulted in several hundred fold increase in gene expression of the GUS gene in transgenic tobacco callus.

The use of a specific promoter, with or without one or more enhancers, however, does not necessarily guarantee desired levels of gene expression in plants. In addition to desired transcription levels, other factors such as improper splicing, polyadenylation and nuclear export can affect accumulation of both mRNA and the protein of interest. Therefore, methods of increasing RNA stability and translational efficiency through mechanisms of post-transcriptional regulation are needed in the art.

With regard to post-transcriptional regulation, it is has been demonstrated that certain 5' and 3' untranslated regions (UTRs) of eukaryotic mRNAs play a major role in translational efficiency and RNA stability, respectively. For example, the 5' and 3' UTRs of tobacco mosaic virus (TMV) and alfalfa mosiac virus (AMV) coat protein mRNAs are known to enhance gene expression in tobacco plants. The 5' and 3' UTRs of the maize alcohol dehydrogenase-1 (adh1) gene are known to be involved in efficient translation in hypoxic protoplasts.

Experiments with various 5' UTR leader sequences demonstrate that various structural features of a 5' UTR can be correlated with levels translational efficiency. Certain 5' UTRs have been found to contain AUG codons which may interact with 40S ribosomal subunits when it scans for the AUG codon at the initiation site, thus decreasing the rate of translation. (Kozak, Mol. Cell. Biol. 7:3438 (1987); Kozak, J. Cell Biol. 108, 209 (1989)). Further, the 5' UTR nucleotide sequences flanking the AUG initiation site on the mRNA may have an impact on translational efficiency. If the context of the flanking 5' UTR is not favorable, part of the 40S ribosomal subunits might fail to recognize the translation start site such that the rate of polypeptide synthesis will be slowed. (Kozak, J. Biol. Chem. 266, 19867-19870 (1991); Pain, Eur. J. Biochem. 236, 747-771 (1996)). Secondary structures of 5' UTRs (e.g., hairpin formation) may also hinder the movement of 40S ribosomal subunits during their scanning process and therefore negatively impact the efficiency of translation. (Sonenberg et al., Nature 334:320 (1988); Kozak, Cell 44:283-292, (1986)). The relative GC content of a 5' UTR sequence has been shown to be an indicator of the stability of the potential secondary structure, with higher levels of GC indicating instability. (Kozak, J. Biol. Chem. 266, 19867-19870 (1991). Longer 5' UTRs may exhibit higher numbers of inhibitory secondary structures. Thus, the translational efficiency of any given 5' UTR is highly dependent upon its particular structure, and optimization of the leader sequence has been shown to increase gene expression as a direct result of improved translation initiation efficiency. Furthermore, significant increases in gene expression have been produced by addition of leader sequences from plant viruses or heat shock genes. (Raju et al., Plant Science 94: 139-149 (1993)).

In addition to 5' UTR sequences, 3' UTR (trailer) sequences of mRNAs are also involved in gene expression. 3' UTRs (also known as polyadenylation elements or adenylation control elements) are known to control the nuclear export, polyadenylation status, subcellular targeting and rates of translation and degradation of mRNA from RNases. In particular, 3' UTRs may contain one or more inverted repeats that can fold into stem-loop structures which act as a barrier to exoribonucleases, as well as interact with proteins known to promoter RNA stability (e.g., RNA binding proteins). (Barkan et al., A Look Beyond Transcription: Mechanisms Determining mRNA Stability and Translation in Plants, American Society of Plant Physiologists, Rockville, Md., pp. 162-213 (1998)). Certain elements found within 3' UTRs may be RNA destabilizing, however. One such example occurring in plants is the DST element, which can be found in small auxin up RNAs (SAURs). (Gil et al., EMBO J. 15, 1678-1686 (1996)). A further destabilizing feature of some 3' UTRs is the presence of AUUUA pentamers. (Ohme-Takagi et al., Pro. Nat. Acad. Sci. USA 90 11811-11815 (1993)).

3' UTRs have been demonstrated to play a significant role in gene expression of several maize genes. Specifically, a 200 base pair 3' sequence has been shown to be responsible for suppression of light induction of the maize small m3 subunit of the ribulose-1,5-biphosphate carboxylase gene (rbc/m3) in mesophyll cells. (Viret et al., Proc Natl Acad Sci USA. 91 (18):8577-81 (1994)). In plants, especially maize, this sequence is not very well conserved. One 3' UTR frequently used in genetic engineering of plants is derived from a nopaline synthase gene (3' nos) (Wyatt et al., Plant Mol Biol 22(5):731-49 (1993)).

In certain plant viruses, such as alfalfa mosaic virus (AMV) and tobacco mosaic virus (TMV), their highly structured 3' UTRs are essential for replication and can be folded into either a linear array of stem-loop structures which contain several high-affinity coat protein binding sites, or a tRNA-like site recognized by RNA-dependent RNA polymerases. (Olsthoorn et al., EMBO J 1; 18(17): 4856-64 (1999); Zeyenko et al., 1994)).

However, there remains a need to identify additional 5' and 3' UTRs for their use in regulating expression of recombinant nucleic acids in transgenic plants because there are no optimal UTR sequences available for every application.

SUMMARY OF THE INVENTION

Provided are methods, vectors and gene constructs for enhancing expression of a recombinant nucleic acid sequence in transgenic plants and plant tissues. According to the present invention, nucleic acid sequences are obtained and/or derived from the 3' untranslated regions of genes encoding ubiquitin proteins and engineered to flank respective portions of a selected coding region of a vector. The vector construct may be introduced into plants and/or plant tissues through conventional or gene targeting procedures, resulting in enhanced expression of the selected coding region. In some embodiments, the selected coding region is a chimeric gene or gene fragment expressing one or more proteins known to impart a level of insecticidal activity to a transgenic plant and/or plant tissue.

In one aspect, provided is a nucleic acid construct comprising at least one structural gene of interest functionally linked to a heterologous promoter and one or more control sequences having 80% identity to a nucleic acid sequence selected from the group consisting of SEQ ID NOS: 1-3, their complements, and combinations thereof.

In one embodiment, the at least one structural gene of interest comprises a gene that confers a non-native phenotype in a plant. In another embodiment, the at least one structural gene of interest comprises a gene that confers insect resistance or herbicide resistance in a plant. In one embodiment, the heterologous promoter does not comprise a viral promoter. In another embodiment, the heterologous promoter does not comprise a plant promoter. In another embodiment, the heterologous promoter comprises a viral promoter. In another embodiment, the heterologous promoter comprises a plant promoter.

In one embodiment, the one or more control sequences having 85%, 90%, 95%, 98%, or 100% identity to a nucleic acid sequence selected from the group consisting of SEQ ID NOS: 1-3, their complements, and combinations thereof. In a further embodiment, the one or more control sequences are selected from the group consisting of SEQ ID NOS: 1-3, their complements, and combinations thereof. In another embodiment, the one or more control sequences are amplifiable using oligonucleotides selected from the group consisting of SEQ ID NOS: 4-15.

In one embodiment, the nucleic acid construct comprises a binary vector for *Agrobacterium*-mediated transformation. In another embodiment, the nucleic acid construct is stably transformed into transgenic plants. In a further embodiment, the plants are monocotyledon plants. In another further embodiment, the plants are dicotyledons plants. In another embodiment, the plants are not monocotyledon plants. In another embodiment, the plants are not dicotyledons plants. In one embodiment, the nucleic acid construct comprises a selectable marker. In a further embodiment, the selectable marker comprises an aryloxyalkanoate dioxygenase. In a further embodiment, the aryloxyalkanoate dioxygenase is AAD-1 or AAD-12.

In another aspect, provided is a vector comprising the nucleic acid construct provided herein. In another aspect, provided is a plant or plant cell transformed with the nucleic acid construct provided herein. In one embodiment, the plant or plant cells comprise an additional structural gene of interest stacked with the at least one gene of interest.

In another aspect, provided is a method for recombinantly producing a peptide or protein comprising functionally linking a heterologous promoter and one or more control sequences having 80% identity to a nucleic acid sequence selected from the group consisting of SEQ ID NOS: 1-3, their complements, and combinations thereof. In another aspect, provided is a method for increasing expression of a gene in a plant or plant cells comprising functionally linking a heterologous promoter and one or more control sequences having 80% identity to a nucleic acid sequence selected from the group consisting of SEQ ID NOS: 1-3, their complements, and combinations thereof.

In one embodiment of the methods provided, the heterologous promoter does not comprise a viral promoter. In another embodiment, the heterologous promoter does not comprise a plant promoter. In another embodiment, the heterologous promoter comprises a viral promoter. In another embodiment, the heterologous promoter comprises a plant promoter. In one embodiment of the methods provided, the one or more control sequences having 85%, 90%, 95%, 98%, or 100% identity to a nucleic acid sequence selected from the group consisting of SEQ ID NOS: 1-3, their complements, and combinations thereof. In a further embodiment, the one or more control sequences are selected from the group consisting of SEQ ID NOS: 1-3, their complements, and combinations thereof. In another embodiment, the one or more control sequences are amplifiable using oligonucleotides selected from the group consisting of SEQ ID NOS: 4-15.

In another aspect, provided is the use of at least one control sequence selected from the group consisting of SEQ ID NOS: 1-3, their complements, and combinations thereof, for expression of transgene in plants. In another aspect, provided is the use of one or more control sequences amplifiable using oligonucleotides selected from the group consisting of SEQ ID NOS: 4-15, for expression of transgene in plants.

BRIEF DESCRIPTION OF THE DRAWINGS

FIG. 1A shows an exemplary control sequence of the present invention Zea mays Ubi1 3'UTR (SEQ ID NO: 1). FIG. 1B shows another exemplary control sequence of the present invention ZMEXP9396.1 (SEQ ID NO: 2). FIG. 1C shows another exemplary control sequence of the present invention ZMEXP9707.1 (SEQ ID NO: 3).

DETAILED DESCRIPTION OF THE INVENTION

Figure 2A:
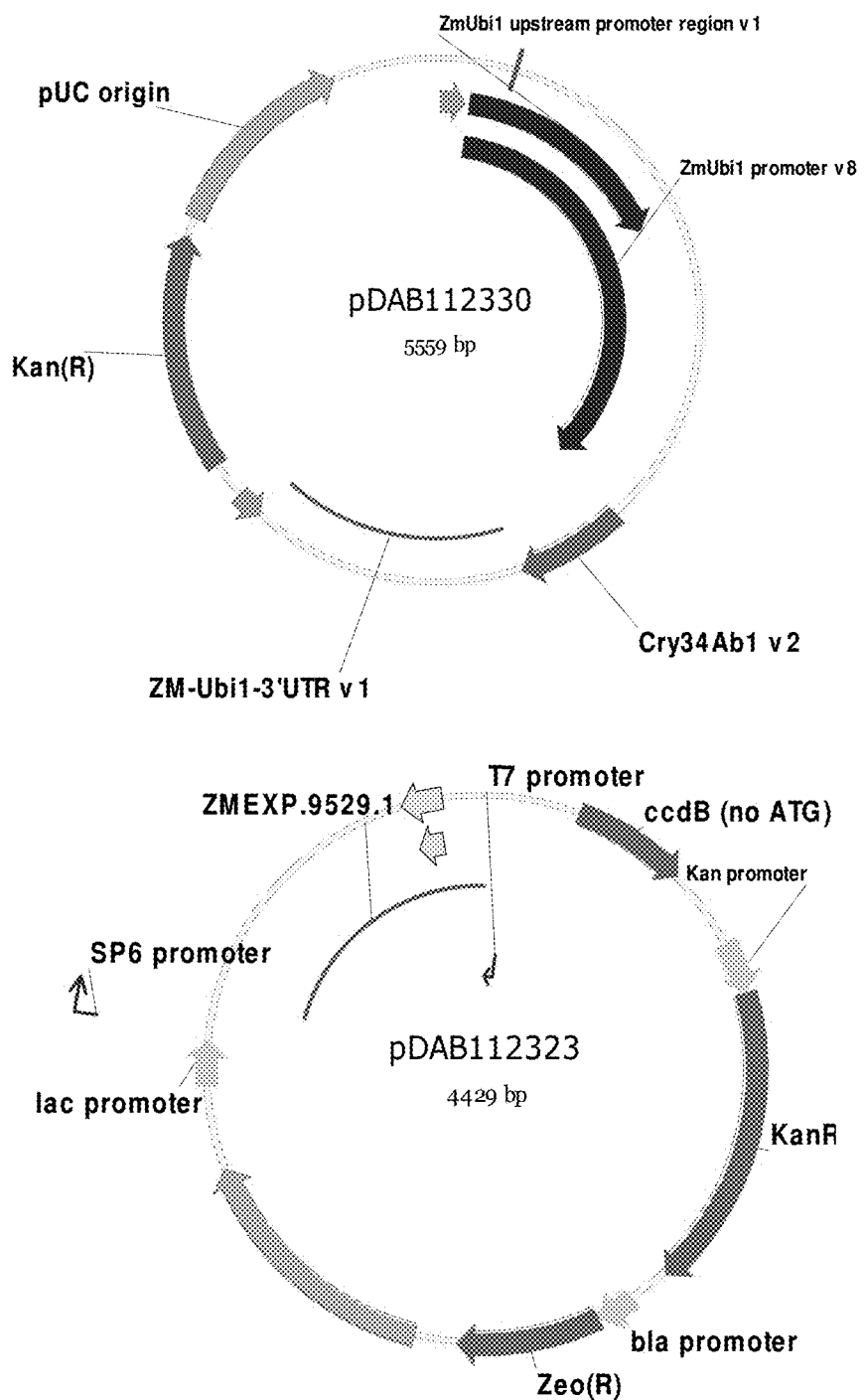
FIG. 2A shows representative plasmid maps of pDAB112330 and pDAB112323.

Provided are compositions and methods for genetically modifying cells, tissues, or organisms using 5' and/or 3' UTR regions isolated or derived from a Zea mays ubiquitin gene. The 5' and/or 3' UTR regions/control sequences of the present invention, when engineered to flank a structural nucleic acid of interest, improve transcription termination, mRNA stability and/or increase translational efficiency of the structural gene of interest in a transgenic plant. Thus, the present invention will facilitate the genetic engineering of plants to express phenotypes of economic or investigative value.

One or both of 5' and 3' UTR regions/control sequences isolated or derived from a Zea mays ubiquitin gene are genetically engineered to flank a structural gene of interest encoding a protein which is expressed recombinantly in a plant, plant cell or plant tissue. The maize Ubi1 3'UTR described is of particular interest for its use in making transgene constructs containing single or multiple genes.

Development of transgenic products requires long-term stable expression of transgenes. Regulatory elements such as promoters and terminators are required in appropriate combination and configuration for the transgenes to be properly expressed. Each transgene requires an exclusive promoter for transcription. In addition, a 3'untranslated region (3'UTR) or terminator is needed for transcription termination and polyadenylation. Proper transcription termination and polyadenylation of mRNA is important for stable expression of transgene. The transcription termination becomes more critical for multigene stacks to avoid transcription read-through into next transgene. Similarly, non-polyadenylated aberrant RNA (aRNA) is a substrate for plant RNA-dependent RNA polymerases (RdRPs) to convert aRNA into double stranded RNA (dsRNA) leading to small RNA production and transgene silencing. Strong transcription terminators therefore are very useful both for single gene and multiple gene stacks. Provided are maize Ubi1 (Ubiquitin1) 3'UTR and its use for making transgene construct.

Plant promoters and 3'UTRs are two basic expression elements needed to build a functional transgene expression or plant transcription unit. Promoters are required to drive transcription while 3'UTRs are needed for transcription termination and polyadenylation of the transcript. The mRNA 3' UTR is required in gene expression for RNA transcript termination and polyadenylation. The 3'UTR also plays a key role in mRNA processing, localization, stability and translation.

Provided are identification and characterization of maize Ubi1 5' and 3'UTRs as control sequences for transgene expression in plants. The Ubi1 3' UTR provided herein can be used with other plant or viral promoter for vector construction and not limited to the maize Ubi1 promoter.

As used herein, the phrase "vector" refers to a piece of DNA, typically double-stranded, which can have inserted into it a piece of foreign DNA. The vector can be for example, of plasmid or viral origin, which typically encodes a selectable or screenable marker or transgenes. The vector is used to transport the foreign or heterologous DNA into a suitable host cell. Once in the host cell, the vector can replicate independently of or coincidental with the host chromosomal DNA. Alternatively, the vector can target insertion of the foreign or heterologous DNA into a host chromosome.

As used herein, the phrase "transgene vector" refers to a vector that contains an inserted segment of DNA, the "transgene" that is transcribed into mRNA or replicated as a RNA within a host cell. The phrase "transgene" refers not only to that portion of inserted DNA that is converted into RNA, but also those portions of the vector that are necessary for the transcription or replication of the RNA. A transgene typically comprises a gene-of-interest but needs not necessarily comprise a polynucleotide sequence that contains an open reading frame capable of producing a protein.

As used herein, the phrase "transformed" or "transformation" refers to the introduction of DNA into a cell. The phrases "transformant" or "transgenic" refers to plant cells, plants, and the like that have been transformed or have undergone a transformation procedure. The introduced DNA is usually in the form of a vector containing an inserted piece of DNA.

As used herein, the phrase "selectable marker" or "selectable marker gene" refers to a gene that is optionally used in plant transformation to, for example, protect the plant cells from a selective agent or provide resistance/tolerance to a selective agent. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include gene for neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including Bar (resistance against BASTA® (glufosinate ammonium), or phosphinothricin (PPT)), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. The phrase "marker-positive" refers to plants that have been transformed to include the selectable marker gene.

Various selectable or detectable markers can be incorporated into the chosen expression vector to allow identification and selection of transformed plants, or transformants. Many methods are available to confirm the expression of selection markers in transformed plants, including for example DNA sequencing and PCR (polymerase chain reaction), Southern blotting, RNA blotting, immunological methods for detection of a protein expressed from the vector, e.g., precipitated protein that mediates phosphinothricin resistance, or other proteins such as reporter genes β-glucuronidase (GUS), luciferase, green fluorescent protein (GFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) EMBO J., 6:2513-2518; DeBlock et al. (1989) Plant Physiol., 91:691-704; Fromm et al. (1990) 8:833-839; Gordon-Kamm et al. (1990) 2:603-618). For example, resistance to glyphosate or sulfonylurea herbicides has been obtained by using genes coding for the mutant target enzymes, 5-enolpyruvylshikimate-3-phosphate synthase (EPSPS) and acetolactate synthase (ALS). Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Enzymes/genes for 2,4-D resistance have been previously disclosed in US 2009/0093366 and WO 2007/053482, the contents of which are hereby incorporated by reference in their entireties.

Other herbicides can inhibit the growing point or meristem, including imidazolinone or sulfonylurea. Exemplary genes in this category code for mutant ALS and AHAS enzyme as described, for example, by Lee et al., EMBO J. 7:1241 (1988); and Miki et al., Theon. Appl. Genet. 80:449 (1990), respectively.

Glyphosate resistance genes include mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include glufosinate (phosphinothricin acetyl transferase (PAT) genes from Streptomyces species, including Streptomyces hygroscopicus and Streptomyces viridichromogenes), and pyridinoxy or phenoxy proprionic acids and cyclohexones (ACCase inhibitor-encoding genes), See, for example, U.S. Pat. No. 4,940,835 to Shah, et al. and U.S. Pat. No. 6,248,876 to Barry et al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene is disclosed in U.S. Pat. No. 4,769,061 to Comai, European patent application No. 0 333 033 to Kumada et al., and U.S. Pat. No. 4,975,374 to Goodman et al., disclosing nucleotide sequences of glutamine synthetase genes which confer resistance to herbicides such as L-phosphinothricin. The nucleotide sequence of a PAT gene is provided in European application No. 0 242 246 to Leemans et al. Also DeGreef et al., Bio/Technology 7:61 (1989), describes the production of transgenic plants that express chimeric bar genes coding for PAT activity. Exemplary of genes conferring resistance to phenoxy proprionic acids and cyclohexones, including sethoxydim and haloxyfop, are the Acc1-S1, Acc1-S2 and Acc1-S3 genes described by Marshall et al., Theon. Appl. Genet. 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893.

Other herbicides can inhibit photosynthesis, including triazine (psbA and 1s+ genes) or benzonitrile (nitrilase gene). Przibila et al., Plant Cell 3:169 (1991), describes the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

For purposes of the present invention, selectable marker genes include, but are not limited to genes encoding: neomycin phosphotransferase II (Fraley et al. (1986) CRC Critical Reviews in Plant Science, 4:1-25); cyanamide hydratase (Maier-Greiner et al. (1991) Proc. Natl. Acad. Sci. USA, 88:4250-4264); aspartate kinase; dihydrodipicolinate synthase (Perl et al. (1993) Bio/Technology, 11:715-718); tryptophan decarboxylase (Goddijn et al. (1993) Plant Mol. Bio., 22:907-912); dihydrodipicolinate synthase and desensitized aspartate kinase (Perl et al. (1993) Bio/Technology, 11:715-718); bar gene (Told et al. (1992) Plant Physiol., 100:1503-1507 and Meagher et al. (1996) and Crop Sci., 36:1367); tryptophan decarboxylase (Goddijn et al. (1993) Plant Mol. Biol., 22:907-912); neomycin phosphotransferase (NEO) (Southern et al. (1982) J. Mol. Appl. Gen., 1:327; hygromycin phosphotransferase (HPT or HYG) (Shimizu et al. (1986) Mol. Cell Biol., 6:1074); dihydrofolate reductase (DHFR) (Kwok et al. (1986) PNAS USA 4552); phosphinothricin acetyltransferase (DeBlock et al. (1987) EMBO J., 6:2513); 2,2-dichloropropionic acid dehalogenase (Buchanan-Wollatron et al. (1989) J. Cell. Biochem. 13D:330); acetohydroxyacid synthase (Anderson et al., U.S. Pat. No. 4,761,373; Haughn et al. (1988) Mol. Gen. Genet. 221:266); 5-enolpyruvyl-shikimate-phosphate synthase (aroA) (Comai et al. (1985) Nature 317:741); haloarylnitrilase (Stalker et al., published PCT application WO87/04181); acetyl-coenzyme A carboxylase (Parker et al. (1990) Plant Physiol. 92:1220); dihydropteroate synthase (sul I) (Guerineau et al. (1990) Plant Mol. Biol. 15:127); and 32 kD photosystem II polypeptide (psbA) (Hirschberg et al. (1983) Science, 222:1346).

Also included are genes encoding resistance to: chloramphenicol (Herrera-Estrella et al. (1983) EMBO J., 2:987-992); methotrexate (Herrera-Estrella et al. (1983) Nature, 303:209-213; Meijer et al. (1991) Plant Mol Bio., 16:807-820 (1991); hygromycin (Waldron et al. (1985) Plant Mol. Biol., 5:103-108; Zhijian et al. (1995) Plant Science, 108: 219-227 and Meijer et al. (1991) Plant Mol. Bio. 16:807-820); streptomycin (Jones et al. (1987) Mol. Gen. Genet., 210:86-91); spectinomycin (Bretagne-Sagnard et al. (1996) Transgenic Res., 5:131-137); bleomycin (Hille et al. (1986) Plant Mol. Biol., 7:171-176); sulfonamide (Guerineau et al. (1990) Plant Mol. Bio., 15:127-136); bromoxynil (Stalker et al. (1988) Science, 242:419-423); 2,4-D (Streber et al. (1989) Bio/Technology, 7:811-816); glyphosate (Shaw et al. (1986) Science, 233:478-481); and phosphinothricin (DeBlock et al. (1987) EMBO J., 6:2513-2518). All references recited in the disclosure are hereby incorporated by reference in their entireties unless stated otherwise.

The above list of selectable marker and reporter genes are not meant to be limiting. Any reporter or selectable marker gene are encompassed by the present invention. If necessary, such genes can be sequenced by methods known in the art.

The reporter and selectable marker genes are synthesized for optimal expression in the plant. That is, the coding sequence of the gene has been modified to enhance expression in plants. The synthetic marker gene is designed to be expressed in plants at a higher level resulting in higher transformation efficiency. Methods for synthetic optimization of genes are available in the art. In fact, several genes have been optimized to increase expression of the gene product in plants.

The marker gene sequence can be optimized for expression in a particular plant species or alternatively can be modified for optimal expression in plant families. The plant preferred codons may be determined from the codons of highest frequency in the proteins expressed in the largest amount in the particular plant species of interest. See, for example, EPA 0359472; EPA 0385962; WO 91/16432; Perlak et al. (1991) Proc. Natl. Acad. Sci. USA, 88:3324-3328; and Murray et al. (1989) Nucleic Acids Research, 17: 477-498; U.S. Pat. Nos. 5,380,831; and 5,436,391, herein incorporated by reference. In this manner, the nucleotide sequences can be optimized for expression in any plant. It is recognized that all or any part of the gene sequence may be optimized or synthetic. That is, fully optimized or partially optimized sequences may also be used.

In addition, several transformation strategies utilizing the *Agrobacterium*-mediated transformation system have been developed. For example, the binary vector strategy is based on a two-plasmid system where T-DNA is in a different plasmid from the rest of the Ti plasmid. In a co-integration strategy, a small portion of the T-DNA is placed in the same vector as the foreign gene, which vector subsequently recombines with the Ti plasmid.

As used herein, the phrase "explant" refers to a removed section of living tissue or organ from one or more tissues or organs of a subject.

As used herein, the phrase "plant" includes dicotyledons plants and monocotyledons plants. Examples of dicotyledons plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein, the phrase "chimeric gene construct" refers to a recombinant nucleic acid comprising genes or portions thereof from more than one organism.

As used herein, the phrase "deletion" refers to a change in either amino acid or nucleotide sequence in which one or more amino acid or nucleotide residues, respectively, are absent.

A 5' and/or 3' Ubi1 UTR(s) of the present invention can be "functionally linked" to a structural nucleic acid sequence of interest if these elements are situated in relation to another such that the 5' and/or 3' Ubi1 UTR(s) can influence mRNA stability, translational efficiency of transcription products of the structural nucleic acid sequence of interest.

As used herein, the phrase "heterologous gene" refers to a gene encoding a protein, polypeptide, RNA, or a portion of any thereof, whose exact amino acid sequence is not normally found in the host cell, but is introduced by standard gene transfer techniques.

As used herein, the phrases "identity" and "similarity" refers to relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (Computational Molecular Biology, Lesk, A. M., ed., Oxford University Press. New York (1988); Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinje, G., Academic Press (1987); and Sequence Analysis Primer, Gribskov, M. and Devereux, J., eds., M Stockton Press, New York (1991)). Methods commonly employed to determine identity or similarity between two sequences include, but are not limited to those disclosed in Carillo, H., and Lipman, D., SIAM J. Applied Math., 48: 1073 (1988). Known methods to determine identity are designed to give the largest match between the two sequences tested. Methods to determine identity and similarity are codified in computer programs. Typical computer program methods to determine identity and similarity between two sequences include: GCG program package (Devereux, J., et al., Nucleic Acids Research 12 (1): 387 (1984)), BLASTP, BLASTN, FASTA and TFASTA (Atschul, S. F. et al., J. Mol. Biol. 215: 403 (1990)).

As used herein, the phrase "insertion" or "addition" refers to a change in an amino acid or nucleotide sequence resulting in the addition of one or more amino acid or nucleotide residues, respectively, as compared to the naturally occurring molecule.

As used herein, the phrase "modified expression" refers to expression in a transgenic plant which is genetically engineered to have one or both of the 5' and/or 3' Ubi1 UTR(s) of the present invention flanking the respective regions of a heterologous structural gene of interest wherein the mRNA levels, protein levels or enzyme specific activity of the structural gene of interest have been altered relative to 1) a native version of the plant, or 2) a transgenic plant harboring the structural gene of interest but not including the one or both of the 5' and 3' Ubi1 UTR(s) as flanking region(s) thereof.

As used herein, the phrase "non-native phenotype" refers to a trait occurring, or influenced by, expression of recombinant DNA in a plant.

As used herein, the phrase "recombinant nucleic acid" refers to nucleic acid that has been derived or isolated from any source, which may be subsequently chemically altered, and later introduced into a transgenic plant. An example of recombinant nucleic acid "derived" from a source, would be a DNA or RNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, the phrase "structural nucleic acid sequence of interest" refers to a sequence of DNA, RNA or synthetic nucleotides that code for a protein. The term "structural nucleic acid of interest" can be used interchangeably herein with the term "structural gene of interest"

As used herein, the phrase "transgenic plant" refers to a plant that contains a foreign nucleotide sequence inserted into either its nuclear genome or organellar genome.

To modify the subject 5' and/or 3' UTR sequence(s) in accordance with the teachings of this invention, exemplary techniques include those for polynucleotide-mediated, site-directed mutagenesis as well as well known techniques for the use of restriction enzymes, PCR amplification and ligase to modify and/or join existing nucleic acid molecules. (See, e.g., Zoller et al., DNA, 3:479-488 (1984); Higuchi et al., *Nucl. Acids Res.*, 16:7351-7367 (1988); Ho et al., *Gene,* 77:51-59 (1989); Horton et al., *Gene,* 77:61 (1989); PCR Technology: Principles and Applications for DNA Amplification, (ed.) Erlich (1989); and U.S. Pat. No. 6,271,360 to Metz et al., *Single-stranded oligodeoxynucleotide mutational vectors* (issued Aug. 7, 2001)). In a preferred embodiment of the invention, one or more stem loop structures are added to provide further protection against mRNA degradation. In one aspect of this embodiment, the additional stem loop structures are derived through PCR amplification. In a further embodiment of the invention, one or more existing stem loop structures are deleted, for example, by the use of site-specific restriction enzymes known to those skilled in the art.

In some embodiments, the 5' and/or 3' Ubi1 UTR(s) of the present invention are used in conjunction with one another with regard to flanking the appropriate regions of one or more structural genes of interest. The present invention, however, is not so limited. One or both of the 5' or 3' Ubi1 UTR(s) of the present invention may thus be used, for example, in conjunction with a UTR native to the structural gene(s) of interest, heterologous to the structural gene(s) of interest and the Ubi1 gene, or in addition to such a native or heterologous UTR.

The 5' and/or 3' Ubi1 UTR(s) for use in the present invention can be isolated by means of nucleic acid hybridization techniques known in the art using, for example, the nucleotide sequences disclosed herein or portions thereof as hybridization probes. Such probes may consist of the entire Ubi1 gene or portions thereof, including the 5' and 3' UTRs identified herein. The subject Ubi1 5' and/or 3' UTR(s) may also be synthetic and obtained using the above described sequences and nucleic acid synthesis techniques known in the art.

The structural nucleic acid sequence of interest is operably linked to 5' and/or 3' UTR control sequences isolated or derived from an Ubi1 gene by known cloning techniques. The structural nucleic acid sequence of interest may be heterologous or homologous to the genes natively presently in the recipient plant, plant cell(s), or plant tissue. In either case, the 5' and/or 3' Ubi1 UTR(s) of the present invention are useful for regulating the translational efficiency of a nucleic acid sequence of interest so as to: increase the half-life of transcribed mRNA; and/or express the protein encoded by the structural nucleic acid sequence of interest in greater abundance in plant tissue than would be expressed without use of the 5' and/or 3' Ubi1 UTR(s) of the present invention. It is further specifically contemplated herein that the present invention is used in a gene construct engineered such that the protein encoded by the structural nucleic acid sequence of interest is expressed only in certain preferred tissue of a plant, such as the roots, leaves or stems, and not in the seed.

The present invention is generally applicable to the expression of structural genes of interest in both monocotyledonous and dicotyledonous plants. This invention is thus suitable for any member of the monocotyledonous (monocot) plant family including, but not limited to, maize, rice, barley, oats, wheat, sorghum, rye, sugarcane, pineapple, yams, onion, banana, coconut, and dates. A preferred application of the present invention is in the production of transgenic maize plants. Dicotyledonous (dicot) species for use with the present invention include, but are not limited to, tobacco, tomato, sunflower, cotton, sugarbeet, potato, lettuce, melon, soybean and canola (rapeseed).

The structural nucleic acid sequence of interest used in constructs of the present invention may be any nucleic acid sequence that provides for, or enhances, a beneficial feature of a resultant transgenic plant. Particularly useful nucleic acid sequences are those that encode proteins or antisense RNA transcripts in order to promote increased nutritional values, higher yields, tolerance to herbicides, insects, or diseases, and the like. More preferably, the nucleic acid sequences will be useful genes which are inherently unstable due to their relatively large size (at least 4-5 kb in length), which is known to render the genes more susceptible to physical, chemical, or enzymatic degradation. Genes inherently unstable due to their size include insecticidal genes from *Xenorhabdus* (see U.S. Pat. No. 6,048,838) and *Photorabdus* (e.g., Toxin A).

In one preferred embodiment of the present invention, one or more structural nucleic acids of interest are flanked by one or more Ubi1 UTRs/control sequences of the present invention which have been "stacked" in relation to one another in a particular crop variety. By use of the phrase "stacked" or "stacking", it is meant herein that multiple structural genes of interest, each structural gene of interest preferably conferring a commercially desirable trait, have been transgenically introduced into a single crop variety (inbred or hybrid). For example, a corn hybrid with stacked genes might contain genes for the insect resistance (e.g., Cry1F B.t. genes) as well as herbicide resistance genes (e.g., glyphosate resistance genes).

In some embodiments, one or more of the Ubi1 UTR(s)/control sequence(s) of the present invention are functionally linked to a Toxin A gene from *Photorabdus*, which is then stacked with one or more insecticide and/or herbicide resistance genes in a single crop variety. In some embodiments, the insecticide gene(s) will be from a *Bacillus thuringiensis* or *Xenorhabdus* spp., and the herbicide gene(s) will be one or more of a glufosinate, glyphosate, imidazolinone, or 2.4-D or sulfonyl urea resistance genes. Of course, any of the "stacked" insecticide or herbicide genes may be functionally linked to the Ubi1 UTRs of the present invention.

The structural nucleic acid sequence of interest may be derived in whole or in part from a bacterial genome or episome, eukaryotic genomic, mitochondrial or plastid DNA, cDNA, viral nucleic acid, or chemically synthesized nucleic acid. It is contemplated that the structural nucleic acid sequence of interest may contain one or more modifications in either the coding region which could affect the biological activity or the chemical structure of the expression product, the rate of expression, or the manner of expression control. Such modifications include, but are not limited to, mutations, insertions, deletions, rearrangements and substitutions of one or more nucleotides. The structural nucleic acid sequence of interest may constitute an uninterrupted coding sequence or it may include one or more introns, bounded by the appropriate plant-functional splice junctions. The structural nucleic acid sequence of interest may be a composite of segments derived from a plurality of sources, naturally occurring or synthetic. The structural nucleic acid sequence of interest may also encode a fusion protein, so long as the experimental manipulations maintain functionality in the joining of the coding sequences.

In carrying out the present invention, cloning techniques are employed so as to obtain a vector containing the 5' and/or 3' Ubi1 UTR(s) flanking the structural gene of interest for subsequent introduction into desired host cells. The 5' and/or 3' Ubi1 UTR(s), structural nucleic acid sequence of interest, and any desired promoters, enhancers, selectable markers, etc. may thus be isolated and cloned into vectors using standard cloning procedures in the art, such as those described by J. Sambrook et al., *Molecular Cloning: A Laboratory Manual*, Cold Spring Harbor Laboratory Press (2d ed., 1989), and Ausubel, F. M. et al. (1989) *Current Protocols in Molecular Biology*, John Wiley & Sons, New York, N.Y. both of which are hereby incorporated by reference.

A wide variety of cloning vectors are available, or can be prepared, where the cloning vector includes a gene construct functional in a desired plant species. Illustrative vectors include, for example, pBR322, pUC series, pACYC184, Bluescript series (Stratagene), and the like. Such vectors are thus commercially available or can be readily prepared for transformation of plant cells. In general, plasmid or viral vectors will contain nucleic acid sequences necessary for both maintenance and expression of a heterologous DNA sequence in a given host. Selection of appropriate elements to optimize expression in any particular species is a matter of ordinary skill in the art utilizing the teachings of this disclosure. Suitable DNA components, selectable marker genes, reporter genes, enhancers, introns, and the like are described by K. Weising et al., *Ann. Rev. Genetics,* 22, 421 (1988).

Typically, the structural nucleic acid sequence of interest and 5' and/or 3' Ubi1 UTR(s) are inserted into an appropriate cloning vector at appropriate restriction site(s) such that the structural gene of interest is operably linked to a desired promoter and 5' and/or 3' Ubi1 UTR(s) are functionally linked to the structural nucleic acid sequence of interest. In preparing the gene constructs of this invention, the various nucleic acid fragments may be manipulated, so as to provide for the nucleic acid sequences in the proper orientation and, as appropriate, in the proper reading frame. Of course, adapters or linkers may be employed for joining nucleic acid fragments or other manipulations may be involved to provide for convenient restriction sites, removal of superfluous DNA, removal of restriction sites, or the like.

The expression of structural genes employed in the present invention may be driven by any number of promoters. Although the endogenous promoter of a structural gene of interest may be utilized herein for transcriptional regulation of the gene, in some embodiments, the promoter is a foreign regulatory sequence. For plant expression vectors, suitable viral promoters include the Cassaya Vein Mosaic Virus promoter (Verdaguer et al., *Plant Mol. Biol.* 31(6):1129-39 (1996); 35S RNA and 19S RNA promoters of Cauliflower Mosaic Virus (CaMV) (Brisson et al., *Nature* 310:511 (1984); Odell et al., *Nature,* 313:810 (1985); the enhanced and double enhanced CaMV35S promoter (Kay et al., *Science* 236:1299-1302 (1987); the full-length transcript promoter from Figwort Mosaic Virus (FMV) (Gowda et al., *J. Cell Biochem.,* 13D: 301, 1989) and the coat protein promoter from TMV (Takamatsu et al., *EMBO J.* 6:307, 1987). Other useful promoters include the light-inducible promoter from the small subunit ribulose 1,5-bisphosphate carboxylase oxygenase (ssRUBISCO) (Coruzzi et al., *EMBO J.,* 3:1671 (1984); Broglie, et al., *Science* 224:838 (1984); rice actin promoter (McElroy et al., *Plant Cell.* 2(2):163-71 (1990); and Adh1 promoter (Dennis et al., *Nucleic Acids Res.* 12(9):3983-4000 (1984)); mannopine synthase promoter (Velten et al., *EMBO J.,* 3:2723, 1984); nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., *Mol. Cell. Biol.* 6:559 (1986); Severin et al., *Plant Mol. Biol.* 15:827, (1990)).

Analysis of the cloning steps can be typically conducted and may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Once the cloning steps have been completed, various techniques exist which allow for the introduction, plant regeneration, stable integration, and expression of foreign recombinant vectors containing heterologous genes of interest in plant cells. One such technique involves acceleration of microparticles coated with genetic material directly into plant cells (U.S. Pat. No. 4,945,050 to Cornell; U.S. Pat. No. 5,141,131 to DowElanco; and U.S. Pat. Nos. 5,538,877 and 5,538,880, both to Dekalb). This technique is commonly referred to as "microparticle bombardment" or "biolistics." Plants may also be transformed using *Agrobacterium* technology (U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to Max Planck, European Patent Applications 604662, 627752 and U.S. Pat. No. 5,591,616 to Japan Tobacco, European Patent Applications 0267159, and 0292435 and U.S. Pat. No. 5,231,019 all to Ciba-Geigy, U.S. Pat. Nos. 5,463,174 and 4,762,785 both to Calgene, and U.S. Pat. Nos. 5,004,863 and 5,159,135 both to Agracetus). Another transformation method involves the use of elongated needle-like microfibers or "whiskers" to transform maize cell suspension cultures (U.S. Pat. Nos. 5,302,523 and 5,464,765 both to Zeneca). In addition, electroporation technology has been used to transform plant cells from which fertile plants have been obtained (WO 87/06614 to Boyce Thompson Institute; U.S. Pat. Nos. 5,472,869 and 5,384,253 both to Dekalb; U.S. Pat. Nos. 5,679,558, 5,641,664, WO9209696 and WO9321335 to Plant Genetic Systems).

Still further techniques for the transformation of plant cells include: direct DNA uptake mechanisms (see Mandel and Higa, *J. Mol. Biol.*, 53:159-162 (1972); Dityatkin et al., *Biochimica et Biophysica Acta*, 281:319-323 (1972); Wigler et al., *Cell*, 16:77 (1979); and Uchimiya et al., In: Proc. 5*th Intl. Cong. Plant Tissue and Cell Culture*, A. Fujiwara (ed.), Jap. Assoc. for Plant Tissue Culture, Tokyo, pp. 507-508 (1982)); fusion mechanisms (see Uchidaz et al., In: *Introduction of Macromolecules Into Viable Mammalian Cells*, Baserga et al. (eds.) Wistar Symposium Series, 1:169-185 (1980)); site specific recombination (see WO/9109957), and various infectious agents (see Fraley et al., *CRC Crit Rev. Plant Sci.*, 4: 1-46 (1986); and Anderson, Science, 226:401-409 (1984)).

The appropriate procedure to transform a selected plant cell may be chosen in accordance with the plant cell used. Based on the experience to date, there appears to be little difference in the expression of genes, once inserted into cells, attributable to the method of transformation itself. Rather, the activity of the foreign gene inserted into plant cells is dependent upon the influence of endogenous plant DNA adjacent the insert. Generally, the insertion of heterologous genes appears to be random using any transformation technique; however, technology currently exists for producing plants with site specific recombination of DNA into plants cells (see WO91/09957).

The particular methods used to transform such plant cells are not critical to this invention, nor are subsequent steps, such as regeneration of such plant cells, as necessary. Any method or combination of methods resulting in the expression of the desired sequence or sequences under the regulatory control of one or more of the subject 5' and/or 3' Ubi1 UTR(s) is acceptable.

Once introduced into the plant tissue, the expression of the structural gene may be assayed in a transient expression system, or it may be determined after selection for stable integration within the plant genome.

Any number of selection systems may be used to recover transformed cell lines. These include, but are not limited to, the herpes simplex virus thymidine kinase (Wigler et al., *Cell* 11:223 (1977)) and adenine phosphoribosyltransferase (Lowy et al., *Cell* 22:817 (1980)) genes that can be employed in tk$^-$ or aprt$^-$ cells, respectively. Also, antimetabolite, antibiotic, or herbicide resistance can be used as the basis for selection; for example, dhfr, which confers resistance to methotrexate (Wigler et al., *Proc. Natl. Acad. Sci.*, 77:3567 (1980)); npt, which confers resistance to the aminoglycosides neomycin and G-418 (Colbere-Garapin et al., *J. Mol. Biol.*, 150:1)(1981)); and ALS (U.S. Pat. No. 5,378,824 to Bedbrook) or PAT (Wehrmann et al., *Nat Biotechnol* 14(10):1274-8 (1996)), which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman and Mulligan, *Proc. Natl. Acad. Sci.*, 85:8047 (1988)). More recently, the use of visible markers has gained popularity with such markers as GFP, anthocyanins, α-glucuronidase and its substrate GUS, luciferase and its substrate luciferin, being widely used not only to identify transformants, but also to quantify the amount of transient or stable protein expression attributable to a specific vector system (Rhodes et al., *Methods Mol. Biol.*, 55:121 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences encoding the polypeptide can be identified by the absence of marker gene function. Alternatively, a marker gene can be placed in tandem with a sequence encoding the polypeptide under the control of a single promoter. Expression of the marker gene in response to induction or selection usually indicates expression of the tandem gene as well.

Alternatively, host cells that contain the nucleic acid sequence encoding the polypeptide of interest (for example, a polypeptide encoded by a nucleic acid of the present invention) and express the polypeptide may be identified by a variety of procedures known to those of skill in the art. These procedures include, but are not limited to, DNA-DNA or DNA-RNA hybridizations and protein bioassay or immunoassay techniques that include membrane, solution, or chip based technologies for the detection and/or quantification of nucleic acid or protein.

The presence of polynucleotide sequences encoding a polypeptide of interest (for example, a polypeptide encoded by a nucleic acid of the present invention) can be detected by DNA-DNA or DNA-RNA hybridization or amplification using probes or portions or fragments of polynucleotides encoding the polypeptide. Nucleic acid amplification based assays involve the use of oligonucleotides or oligomers based on the sequences encoding the polypeptide to detect transformants containing DNA or RNA encoding the polypeptide. As used herein "oligonucleotides" or "oligomers" refer to a nucleic acid sequence of at least about 10 nucleotides and as many as about 60 nucleotides, preferably about 15 to 30 nucleotides, and more preferably about 20-25 nucleotides, that can be used as a probe or amplimer.

A variety of protocols for detecting and measuring the expression of a polypeptide (for example, a polypeptide encoded by a nucleic acid of the present invention), using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the polypeptide is preferred, but a competitive binding assay may be employed. These and other assays are described, among other places, in Hampton et al., *Serological Methods, a Laboratory Manual*, APS Press, St Paul, Minn. (1990), and Maddox et al., *J. Exp. Med.*, 158:1211 (1983).

A wide variety of labels and conjugation techniques are known by those skilled in the art and may be used in various nucleic acid and amino acid assays. Means for producing labeled hybridization or PCR probes for detecting sequences related to polynucleotides encoding a polypeptide of interest include oligonucleotide labeling, nick translation, end-labeling or PCR amplification using a labeled nucleotide. Alternatively, the sequences encoding the polypeptide, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.), Promega Corporation (Madison, Wis.) and U.S. Biochemical Corp. (Cleveland, Ohio). Suitable reporter molecules or labels, that may be used, include radionuclides, enzymes, fluorescent, chemiluminescent, or chromogenic agents as well as substrates, cofactors, inhibitors, magnetic particles, and the like.

Techniques are known for the in vitro culture of plant tissue, and, in a number of cases, for regeneration into whole plants. The appropriate procedure to produce mature transgenic plants may be chosen in accordance with the plant species used. Regeneration varies from species to species of plants. Efficient regeneration will depend upon the medium, on the genotype, and on the history of the culture. Once whole plants have been obtained, they can be sexually or clonally reproduced in such a manner that at least one copy of the sequence is present in the cells of the progeny. Seed from the regenerated plants can be collected for future use, and plants grown from this seed. Procedures for transferring the introduced gene from the originally transformed plant into commercially useful cultivars are known to those skilled in the art.

Particular embodiments of this invention are further exemplified in the Examples. However, those skilled in the art will readily appreciate that the specific experiments detailed are only illustrative of the invention as described more fully in the claims which follow thereafter.

EXAMPLES

Example 1

The Ubi1 3'UTR sequence is PCR amplified using a forward primer annealing to the sequence immediate downstream of the maize Ubi1 gene translation stop codon. A reverse primer is designed that annealed to the sequence 910 bp downstream of the stop codon. This 910 bp sequence includes the 3'UTR and downstream non transcribed region potentially required for proper transcription. The primer sequences are shown in Table 1. The PCR products are cloned into topo vector using an Invitrogen Topo kit. The 3'UTR insert is sequenced confirmed using maize B73 as a reference genome.

Figure 2B:
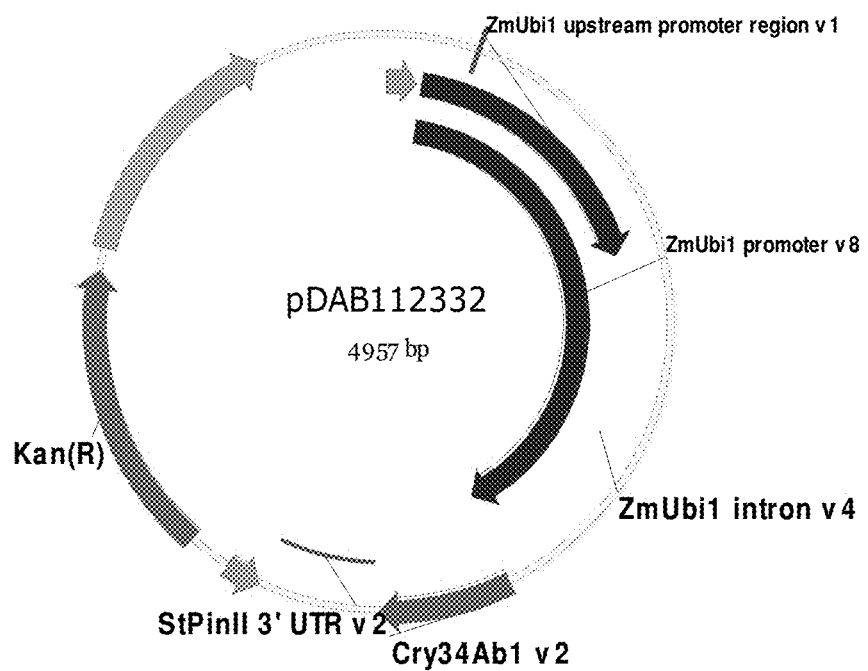
FIG. 2B shows a representative plasmid map of pDAB112332.

The 3'UTR is further PCR amplified to add ~15 nt overhangs on the ends to obtain the sequence compatible to seamless cloning (Invitrogen, Catalog no. A13288). A seamless cloning reaction is used to create the vector pDAB112330 (ZmUbi1 Promoter v8/Cry34Ab1 v2/maizeUbi1 3'UTR v1, FIG. 2A). Another vector containing Zea mays (Zm) Ubiquitin (Ubi) Promoter v8/Cry34Ab1 v2/St PinII 3'UTR v2 (pDAB112332, FIG. 2B) is also built to compare the expression of the Ubi1 3'UTR with that of potato PinII 3'UTR.

TABLE 1

Primer sequences used to amplify ZM Ubi1 3'UTR

| Primer Name | Sequence | SEQ ID NO: |
|---|---|---|
| ASP/ZM Ubi1-3'UTR/1-910 | 5'-GTCACGACTC-ATGGCCAAAA-GT-3' | SEQ ID NO: 4 |
| SP/ZM Ubi1-3'UTR/1-910 | 5'-GTCATGGGTC-GTTTAAGCTG-CC-3' | SEQ ID NO: 5 |
| 3'ZM-Ubi1-3'UTR v1-seamless | 5'-TAGCTTAATC-ACCTAGAGCT-CGTCATGGGT-CGTTTAAGCT-GCCGA-3' | SEQ ID NO: 6 |
| 5'ZM-Ubi1-3'UTR v1-seamless | 5'-AAGCTGGGTC-TAGATGTCAC-GACTCATGGC-CAAAAGTGA-3' | SEQ ID NO: 7 |

Figure 3:
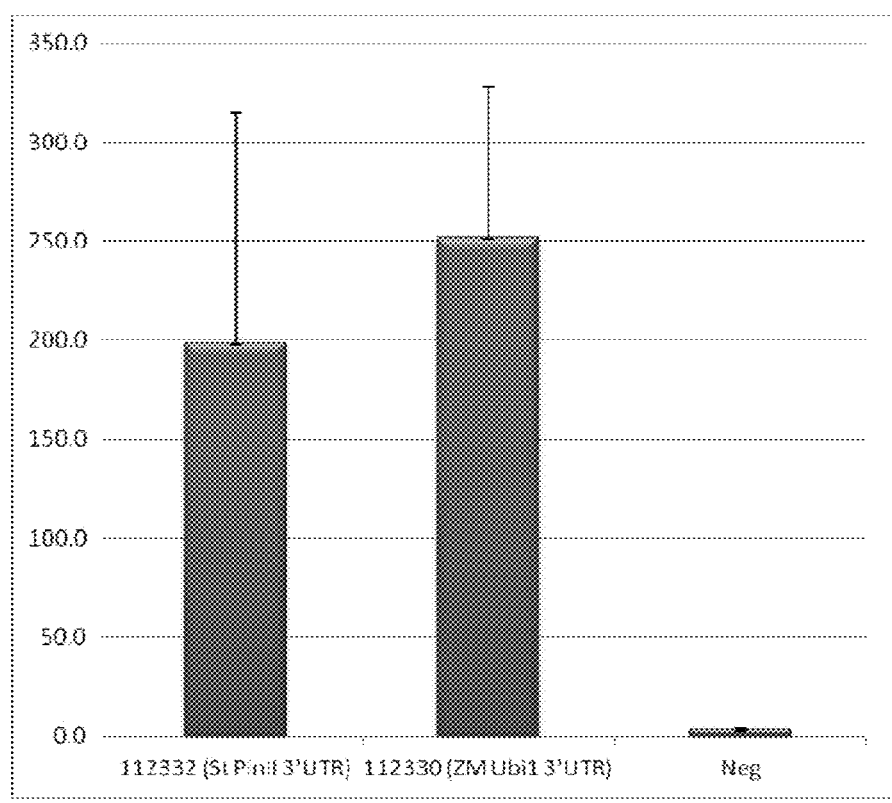
FIG. 3 shows an exemplary expression results from different nucleic acid constructs including St PinII 3'UTR (pDAB112332) and Zea mays Ubi1 3'UTR (pDAB112330), as well as a negative control.

Transient Expression Testing: the transient expression is tested using particle bombardment of immature maize (B104) embryos harvested 10-12 days post pollination. Twenty embryos are used per treatment and three replicates are used. ELISA is carried out after overnight incubation of embryos following particle bombardment. FIG. 3 shows that good protein expression levels are obtained from nucleic acid constructs comprising combination with either potato PinII or maize Ubi1 3' UTR, where maize Ubi1 3'UTR provides better expression. Neg is non-shot control.

Example 2

An expression comparison similar to Example 1 is carried out between the control sequences ZMEXP9396.1, ZMEXP9707.1, and St PinII 3'UTR.

Figure 4:
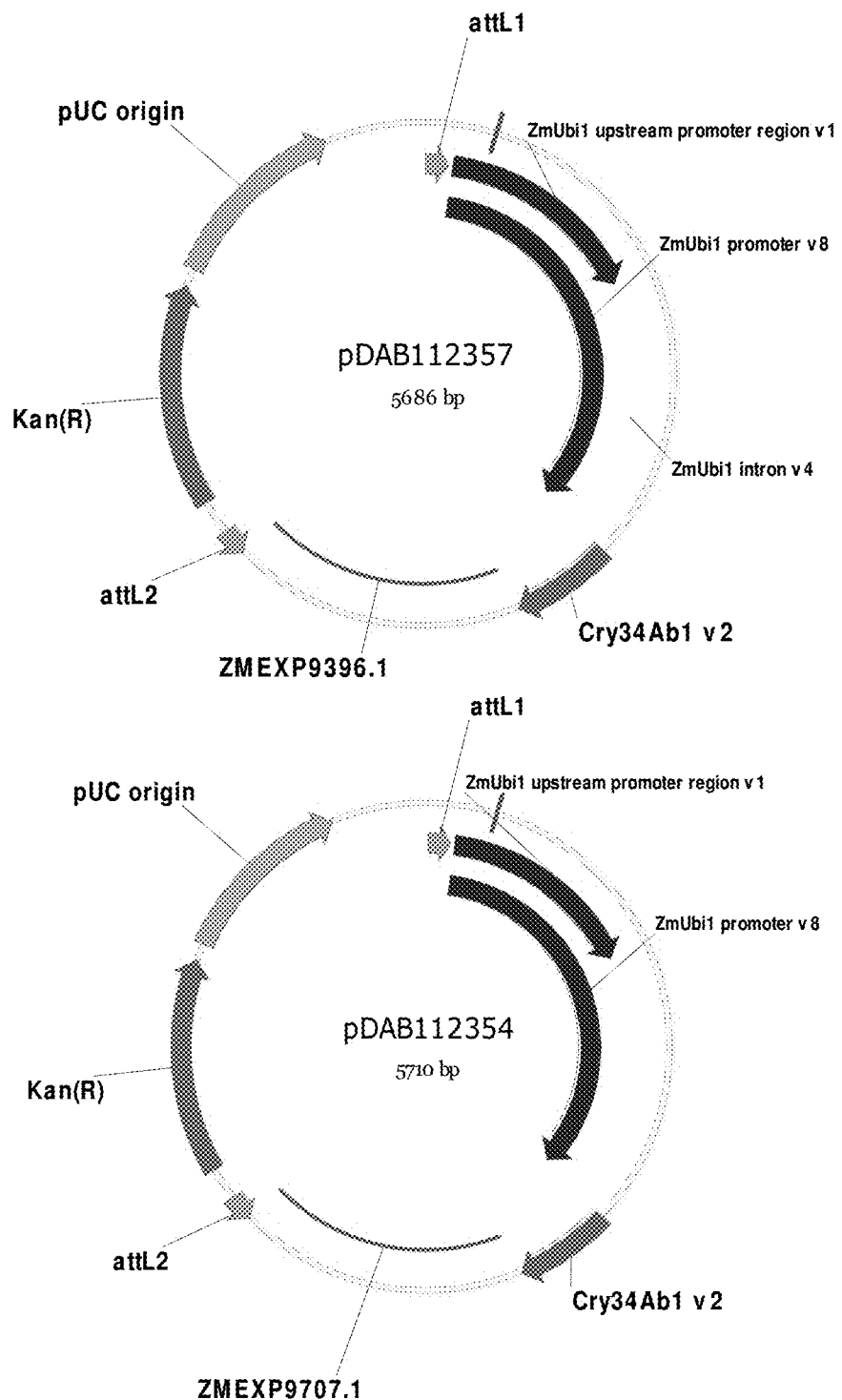
FIG. 4 shows representative plasmid maps of pDAB112357 (ZMEXP9396.1) and pDAB112354 (ZMEXP9707.1).

FIG. 4 shows representative plasmid maps of pDAB112357 (ZMEXP9396.1) and pDAB112354 (ZMEXP9707.1). The Cry34Ab1 gene is used for testing expression of a transgene. The expression level of Cry34Ab1 can be measured by methods known in the art.

Figure 5:
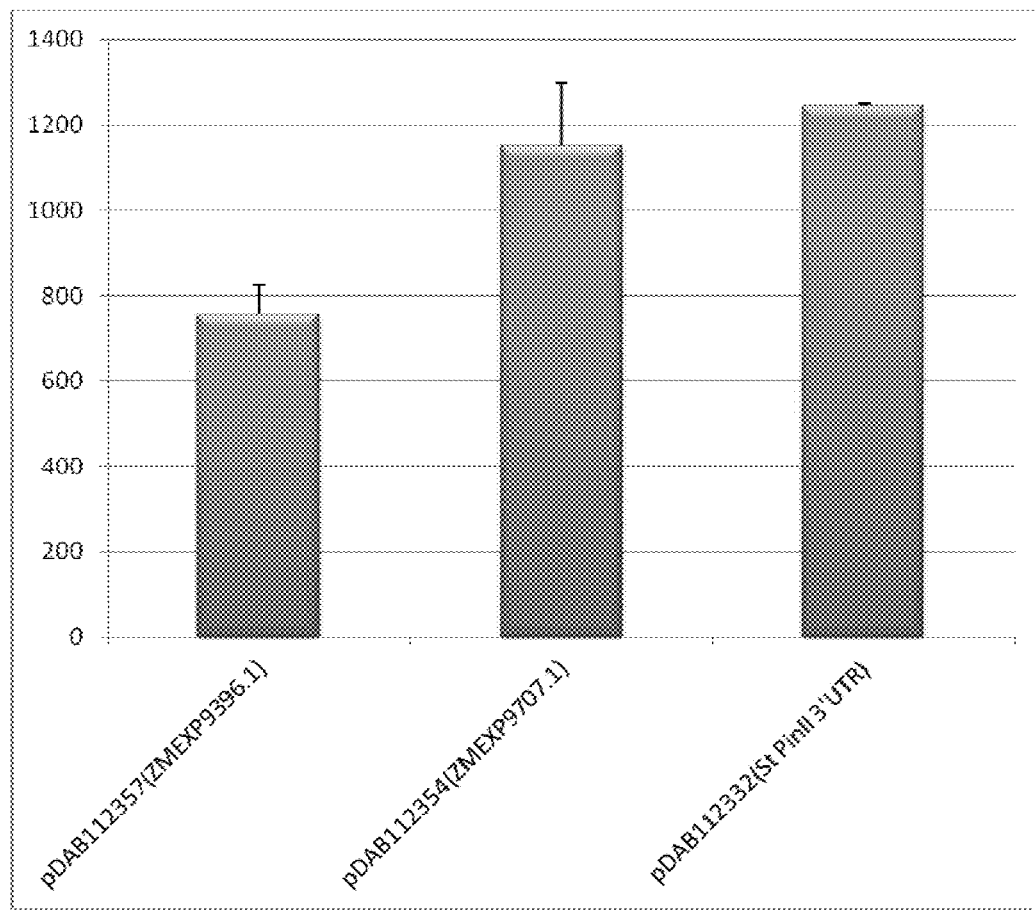
FIG. 5 shows exemplary expression results from different nucleic acid constructs including pDAB112357 (ZMEXP9396.1), pDAB112354 (ZMEXP9707.1), and pDAB112332 (St PinII 3'UTR), where all three constructs provide comparable good expression levels. Cry34 expression levels are shown in ng/ml.

FIG. 5 shows exemplary expression results from different nucleic acid constructs including pDAB112357 (ZMEXP9396.1), pDAB112354 (ZMEXP9707.1), and pDAB112332 (St PinII 3'UTR). All three constructs provide comparable good expression for Cry34Ab1.

Table 2 lists primers used to amplify the control sequences ZMEXP9396.1, ZMEXP9707.1, and Zea mays Ubi1 3'UTR.

TABLE 2

Primers used in this example.

| Primer Name | Sequence and SEQ ID NO. |
|---|---|
| ASP/ZM Ubi1-3'UTR/1-910 | 5'-GTCACGACTC-ATGGCCAAAA-GT-3' (SEQ ID NO: 4) |
| SP/ZM Ubi1-3'UTR/1-910 | 5'-GTCATGGGTC-GTTTAAGCTG-CC-3' (SEQ ID NO: 5) |
| 3'ZM-Ubi1-3'UTR v1-seamless | 5'-TAGCTTAATC-ACCTAGAGCT-CGTCATGGGT-CGTTTAAGCT-GCCGA-3' (SEQ ID NO: 6) |
| 5'ZM-Ubi1-3'UTR v1-seamless | 5'-AAGCTGGGTC-TAGATGTCAC-GACTCATGGC-CAAAAGTGA-3' (SEQ ID NO: 7) |
| ZMEXP9396.1F | 5'-AGTTCTAGCA-GCTTGCCTGC-ATG-3' (SEQ ID NO: 8) |

TABLE 2-continued

Primers used in this example.

| Primer Name | Sequence and SEQ ID NO. |
|---|---|
| ZMEXP9396.1R | 5'-CTATTGTTGA-TTAGCCTTAC-AAATCGC-3' (SEQ ID NO: 9) |
| ZMEXP9396.1F-seamless | 5'-TAGCTTAATC-ACCTAGAGCT-CAGTTCTAGC-AGCTTGCCTG-CA-3' (SEQ ID NO: 10) |
| ZMEXP9396.1R-seamless | 5'-AAGCTGGGTC-TAGATCTATT-GTTGATTAGC-CTTACA-3' (SEQ ID NO: 11) |
| ZMEXP9707.1F | 5'-GCTCAGCTTC-TCCATTTGCA-TGGTC-3' (SEQ ID NO: 12) |
| ZMEXP9707.1R | 5'-ACGCGTCATT-GCTACAGGTT-CGCA-3' (SEQ ID NO: 13) |
| ZMEXP9707.1F-seamless | 5'-TAGCTTAATC-ACCTAGAGCT-CGCTCAGCTT-CTCCATTTGC-AT-3' (SEQ ID NO: 14) |
| ZMEXP9707.1R-seamless | 5'-AAGCTGGGTC-TAGATACGCG-TCATTGCTAC-AGGTTC-3' (SEQ ID NO: 15) |

Example 3

Vector Construction: The 3'UTR sequences are PCR amplified using a forward primer annealing to the sequence immediate downstream of the corresponding maize gene translation stop codon. A reverse primer is designed that annealed to the sequence approximately 900-1000 bp downstream of the stop codon. This approximate 1000 bp sequence includes the 3'UTR and downstream non transcribed region potentially required for proper transcription. The PCR products are cloned into topo vector using an Invitrogen Topo kit. The 3'UTR insert is sequenced confirmed using maize B73 as a reference genome.

The 3'UTR is further PCR amplified to add about 15 nt overhangs on the ends to obtain the sequence compatible to seamless cloning (Invitrogen, Catalog no. A13288). A seamless cloning reaction is used to create the Gateway® (INVITROGEN) Entry vectors pDAB112330 (ZmUbi1 Promoter v8/Cry34Ab1 v2/ZmUbi1 3'UTR v1; see FIG. 2A), pDAB112354 (ZmUbi v8/Cry34Abi v2/ZMEXP9707.1 3'UTR; see FIG. 4), and pDAB112357 (ZmUbi v8/Cry34Abi v2/ZMEXP9396.1 3'UTR; see also FIG. 4). Another vector containing Zea mays (Zm) Ubiquitin (Ubi) Promoter v8/Cry34Ab1 v2/St PinII 3'UTR v2 (pDAB112332, FIG. 2B) is also built to compare the expression of the Ubi1 3'UTR with that of potato PinII 3'UTR.

Figure 6:
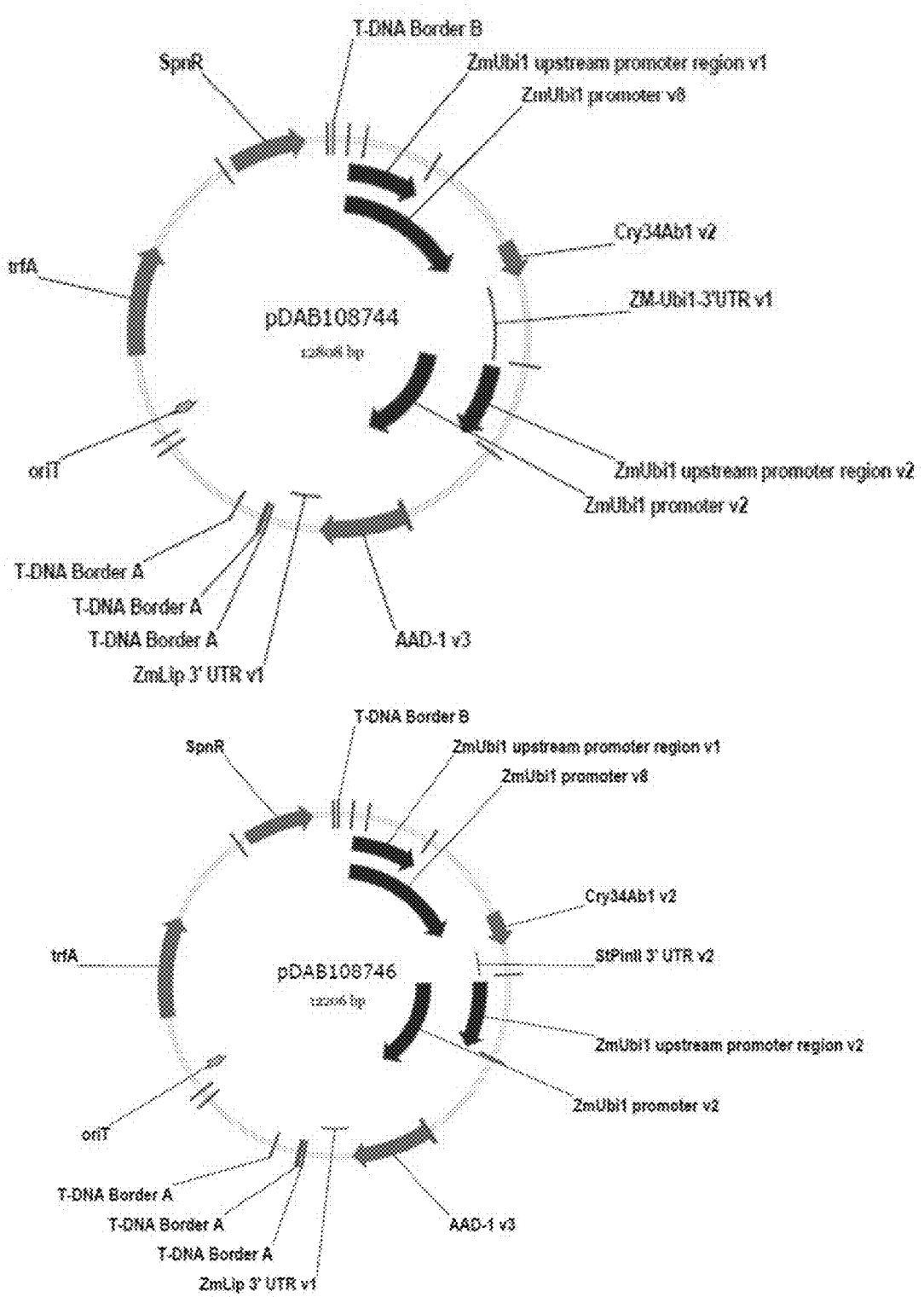
FIG. 6 shows representative plasmid maps of pDAB108744 and pDAB108746.
Figure 7:
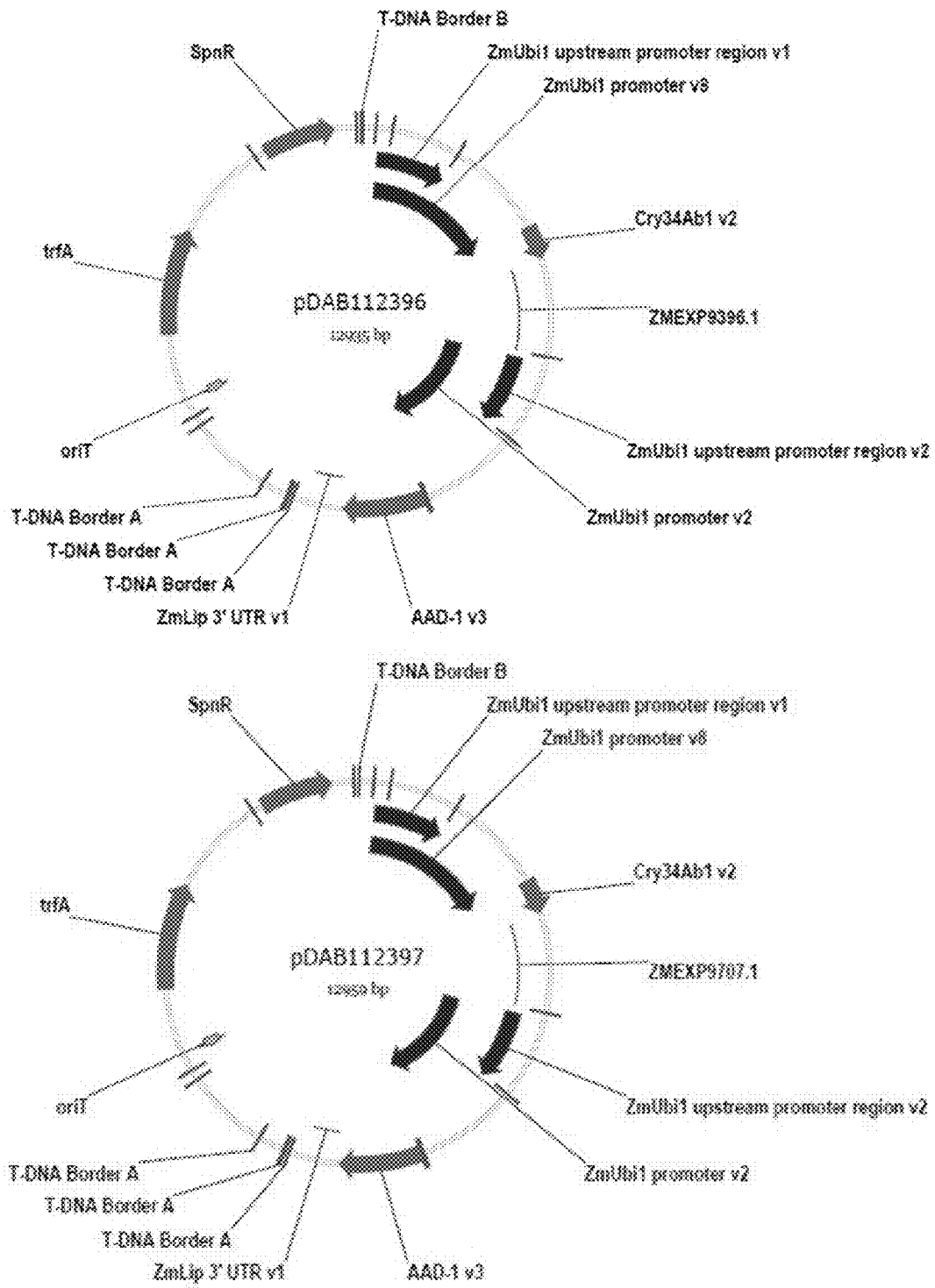
FIG. 7 shows representative plasmid maps of pDAB112396 and pDAB112397.
Figure 8A:
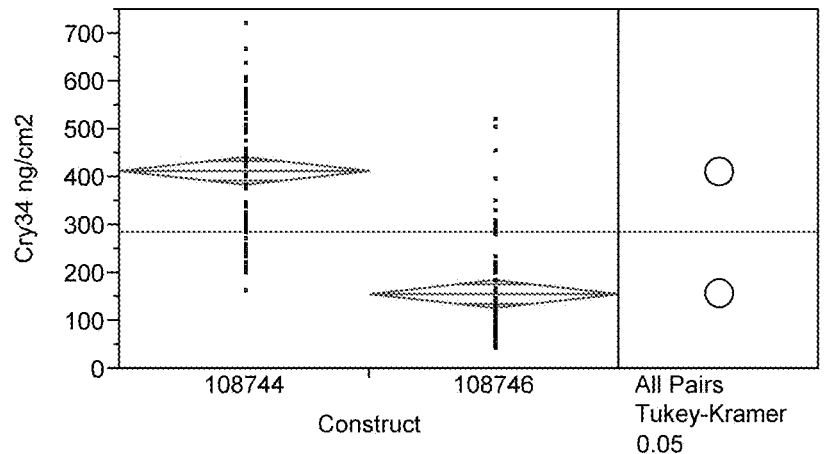
FIG. 8 shows representative T1 expression data (V4 leaf) relating to Zm Ubi1 3'UTR with constructs pDAB108744 and pDAB108746.
Figure 8B:
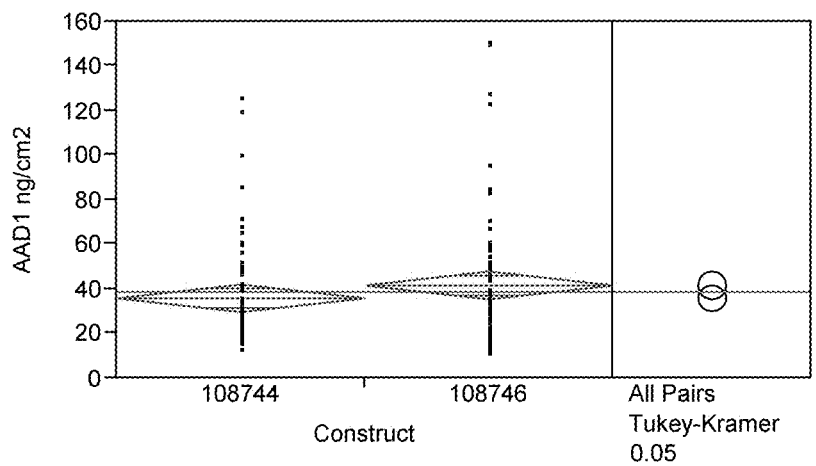
Figure 9A:
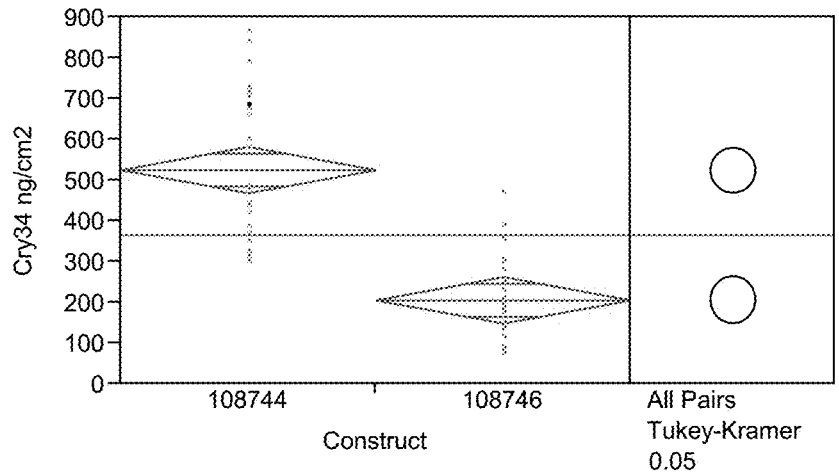
FIG. 9 shows representative T1 expression data (V12 leaf) relating to Zm Ubi1 3'UTR with constructs pDAB108744 and pDAB108746.
Figure 9B:
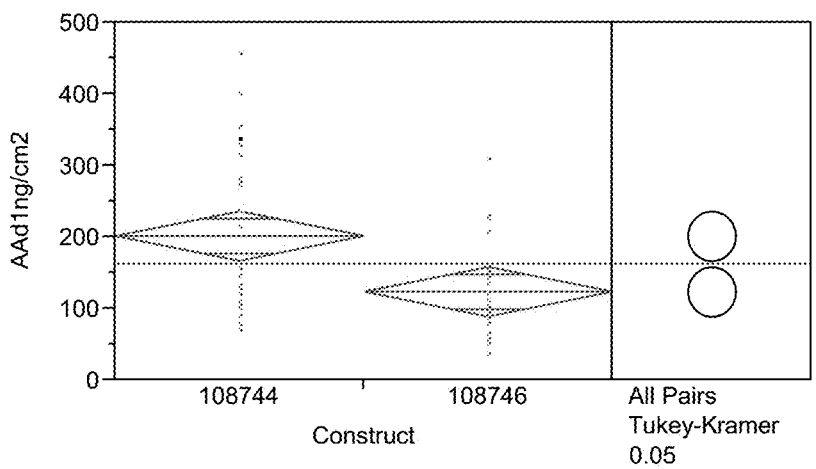
Figure 10:
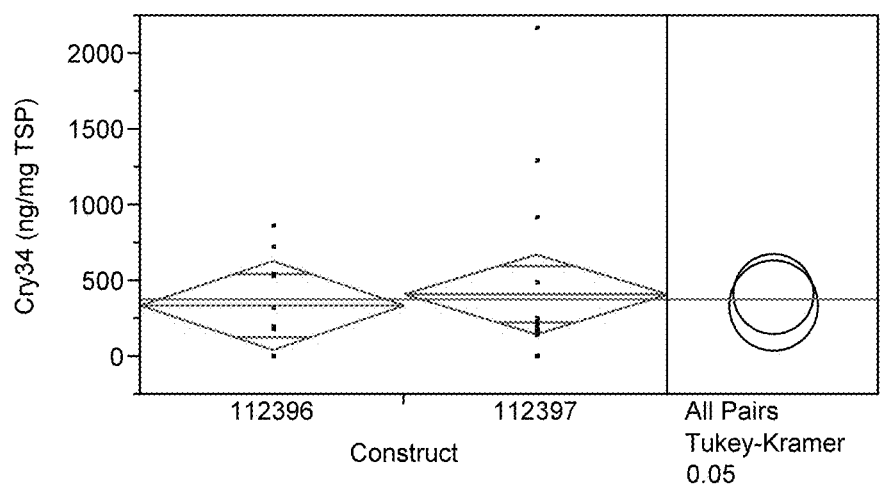
FIG. 10 shows representative T0 expression data (V4 leaf) relating to corn 3'UTR other than Ubi1 with constructs pDAB112396 and pDAB112397.

Transformation/expression vectors for Agrobacterium-mediated maize embryo transformation are constructed through the use of standard cloning methods and Gateway® recombination reactions employing a typical destination binary vector (pDAB104153) and entry vectors as described above. Binary destination vector pDAB104153 comprises a herbicide tolerance gene (aryloxyalknoate dioxygenase (AAD-1); U.S. Pat. No. 7,838,733, and Wright et al. (2010) Proc. Natl. Acad. Sci. U.S.A. 107:20240-20245) under the expression control of a Zea mays (Zm) Ubiquitin (Ubi) Promoter. A fragment comprising a 3'UTR from a maize lipase gene (ZmLip 3'UTR, U.S. Pat. No. 7,179,902) is used to terminate transcription of the PAT mRNA. The Gateway® recombination reaction is used for the ZmUbi1v8/Cry34Abi v2/3'UTR expression cassette, as described in four entry vectors above, between the T-DNA borders and upstream of the AAD-1 expression cassette. The four final expression vectors pDAB108744, pDAB108746, pDAB112396 and pDAB112397 are shown in FIGS. 6 and 7.

Transformation of Agrobacterium tumefaciens: The binary vectors are transformed into Agrobacterium tumefaciens strain DAt13192 ternary (published in WO 2012/016222 international PCT application). Binary plasmid DNA is isolated from bacterial colonies and confirmed using restriction enzyme digestions.

Corn transformation: Glycerol stocks of the project vectors in the host Agrobacterium tumefaciens strain DAt13192 (RecA minus ternary strain) are obtained from the DAS Recombinant Culture Collection (RCC). Agrobacterium cultures are streaked from glycerol stocks onto AB minimal medium (media ID: AT00002247) and incubated at 20° C. in dark for three days. Agrobacterium cultures are then streaked onto a plate of YEP medium (media ID: AT00002245) and incubated at 20° C. in dark for one day.

A mixture of Inoculation medium (media ID: ZM00002914) and acetosyringone is prepared in a volume appropriate to the number of constructs in the experiment. Inoculation medium is pipetted into a sterile, disposable, 250 ml flask. 1 M stock solution of acetosyringone in 100% dimethyl sulfoxide (stock recipe ID: EPS000400) is added to the flask containing inoculation medium in a volume appropriate to make a final acetosyringone concentration of 200 µM. Exemplary volumes of Inoculation medium and 1 M acetosyringone stock solution are listed in Table 3.

TABLE 3

Exemplary volumes of inoculation medium/acetosyringone for different number of constructs

| No. of constructs to be prepared | Volume of inoculation medium (mL) | Volume of 1M acetosytingone stock solution (µl) |
|---|---|---|
| 1 | 50 | 10 |
| 2 | 100 | 20 |
| 3 | 150 | 30 |
| 4 | 200 | 40 |
| 5 | 250 | 50 |

For each construct, 1-2 loops of Agrobacterium from the YEP plate are suspended in 15 ml of the inoculation medium/acetosyringone mixture inside a sterile, disposable, 50 ml centrifuge tube and the optical density of the solution at 600 nm (O.D.$_{600}$) is measured in a spectrophotometer. The suspension is then diluted down to 0.25-0.35 O.D.600 using additional Inoculation medium/acetosyringone mixture. The tube of Agrobacterium suspension is then placed horizontally on a platform shaker set at about 75 rpm at room temperature for between 1 and 4 hours before use.

Ear sterilization and embryo isolation: Ears from Zea mays cultivar B104 are produced in Indianapolis greenhouse facilities and harvested 10-12 days post pollination. Harvested ears are de-husked and surface-sterilized in a 20% solution of commercial bleach (Ultra Clorox® Germicidal Bleach, 6.15% sodium hypochlorite) and two drops of Tween 20, for twenty minutes, followed by three rinses in sterile, deionized water inside a laminar flow hood. Immature zygotic embryos (1.8-2.2 mm long) are aseptically excised from each ear and distributed into one or more micro-centrifuge tubes containing 2.0 ml of Agrobacterium suspension into which 2 µl of 10% Break-Thru® S233 surfactant is added Agrobacterium co-cultivation: Upon completion of the embryo isolation activity the tube of embryos is closed and placed on a rocker platform for 5 minutes. The contents of the tube are then poured out onto a plate of co-cultivation medium (media ID: ZM00003237) and the liquid *Agrobacterium* suspension is removed with a sterile, disposable, transfer pipette. The co-cultivation plate containing embryos is placed at the back of the laminar flow hood with the lid ajar for thirty minutes; after which time the embryos are oriented with the scutellum facing up using a microscope. The co-cultivation plate with embryos is then returned to the back of the laminar flow hood with the lid ajar for another fifteen minutes. The plate is then closed, sealed with 3M Micropore tape, and placed in an incubator at 25° C. with 24 hours/day light at approximately 60 µmol $m^{-2}$ $s^{-1}$ light intensity.

Callus Selection and Regeneration of Transgenic Events: Following the co-cultivation period, embryos are transferred to Resting medium (media ID: ZM00003262). Up to 36 embryos are moved to each plate. The plates are placed in clear boxes and incubated at 27° C. with 24 hours/day light at approximately 50 µmol $m^{-2}$ $s^{-1}$ light intensity for 7-10 days. Callused embryos are then transferred onto Selection I medium (media ID: ZM00003233). Up to 18 callused embryos are moved to each plate of Selection I. The plates are placed in clear boxes and incubated at 27° C. with 24 hours/day light at approximately 50 µmol $m^{-2}$ $s^{-1}$ light intensity for 7 days. Callused embryos are then transferred to Selection II medium (media ID: ZM00003234). Up to 12 callused embryos are moved to each plate of Selection II. The plates are placed in clear boxes and incubated at 27° C. with 24 hours/day light at approximately 50 µmol $m^{-2}$ $s^{-1}$ light intensity for 14 days.

At this stage resistant calli are moved to Pre-Regeneration medium (media ID: ZM00003235). Up to 9 calli are moved to each plate of Pre-Regeneration. The plates are placed in clear boxes and incubated at 27° C. with 24 hours/day light at approximately 50 µmol $m^{-2}$ $s^{-1}$ light intensity for 7 days. Regenerating calli are then transferred to Regeneration medium in Phytatrays™ (media ID: ZM00003236) and incubated at 28° C. with 16 hours light/8 hours dark per day at approximately 150 µmol $m^{-2}$ $s^{-1}$ light intensity for 7-14 days or until shoots develop. Up to 5 calli are placed in each Phytatray™. Small shoots with primary roots are isolated and transferred to Shoot Elongation medium (media ID: ZM00003269). Rooted plantlets about 6 cm or taller are transplanted into soil and moved out to a growth chamber for hardening off.

Transfer and Establishment of Plants in the Greenhouse: Transgenic plants are assigned unique identifiers through the TOPAZ database and transferred on a regular basis to the greenhouse. Plants are transplanted from Phytatrays™ to small pots (T. O. Plastics, 3.5" SVD, 700022C) filled with growing media (Premier Tech Horticulture, ProMix BX, 0581 P) and covered with humidomes to help acclimate the plants. Plants are placed in a Conviron growth chamber (28° C./24° C., 16-hour photoperiod, 50-70% RH, 200 µmol $m^{-2}$ $s^{-1}$ light intensity) until reaching V3-V4 stage. This aided in acclimating the plants to soil and harsher temperatures. Plants are then moved to the greenhouse (Light Exposure Type: Photo or Assimilation; High Light Limit: 1200 µmol $m^{-2}$ $s^{-1}$ photosynthetically active radiation (PAR); 16-hour day length; 27° C. Day/24° C. Night) and transplanted from the small pots to 5.5 inch pots. The T0 plants are backcrossed to B104 to obtain T1 hemizygous seed.

ELISA quantification of AAD-1 and Cry34 proteins: Enzyme Linked Immunosorbant Assays (ELISA) are used to measure the production of AAD-1 and Cry34 proteins in maize cells or stably transformed tissues. AAD-1 protein is quantified using kits from ACADIA BIOSCIENCES (Cat #ABS-041) and Agdia, Inc (Cat#04500/4800), respectively.

The ELISAs are performed using multiple dilutions of plant extracts and using the reagents and instructions according to the suppliers.

TABLE 4

List of forward and reverse nucleotide primers and fluorescent probes used for transgene copy number and relative expression detection.

| Gene Detected | Oligo-nucleotide ID* | Sequence |
|---|---|---|
| AAD-1 | AAD1F | TGTTCGGTTCCCTCTACCAA (SEQ ID NO: 16) |
|  | AAD1R | CAACATCCATCACCTTGACTGA (SEQ ID NO: 17) |
|  | AAD1P (FAM* Probe) | CACAGAACCGTCGCTTCAGCAACA (SEQ ID NO: 18) |
| PAT | TQ.8v6.1.F | GCCATACCCTCCAGTTG (SEQ ID NO: 19) |
|  | TQ.8v6.1 (MGB.P) | 5-/56-FAM/CCGAATCCAACGGCT TCA/MGB(SEQ ID NO: 20) |
|  | TQ.8v6.1.R | GCCGTTGATGGAGTAGTAGATGG (SEQ ID NO: 21) |
| Spec | SPC1A | CTTAGCTGGATAACGCCAC (SEQ ID NO: 22) |
|  | SPC1S | GACCGTAAGGCTTGATGAA (SEQ ID NO: 23) |
|  | TQSPC (FAM Probe) | CGAGATTCTCCGCGCTGTAGA (SEQ ID NO: 24) |
| Maize Invertase | InvertaseF | TGGCGGACGACGACTTGT (SEQ ID NO: 25) |
|  | InvertaseR | AAAGTTTGGAGGCTGCCGT (SEQ ID NO: 26) |
|  | InvertaseP (HEX Probe) | CGAGCAGACCGCCGTGTACTT (SEQ ID NO: 27) |

*Fluorescent probe labels are:
FAM = 6-Carboxy Fluorescein Amidite;
HEX = hexachloro-fluorescein;
MGB = Minor Groove Binder.

Plant protein extraction: Proteins are extracted from 4 leaf discs (totaling 1.3 $cm^2$) or 40 immature embryos (for transient expression studies) in 0.6 mL of PBST (PBS buffer containing 0.05% Tween 20) containing either 0.5% BSA (for AAD-1 extraction) or 1% PVP-40 (PolyVinylPyrrolidone; for Cy34). A 2 mm steel bead is added, the tubes are capped and secured in a GENO/GRINDER (CERTIPREP; Metuchen, N.J.), and shaken for 5 min at 1500 rpm. Tubes are centrifuged at 4000 rpm for 7 min at 4° C., and supernatants containing the soluble proteins are stored at −80° C. until used. Total protein concentrations are determined using a PIERCE 660 nm Protein Assay kit (THERMO SCIENTIFIC; Rockford, Ill.) according to supplier's instructions.

Hydrolysis Probe qPCR for copy number analysis: Various types of molecular analyses are employed to screen for low copy, simple events. Leaf tissue is collected from rooted putative transgenic plants before transplanting to soil. DNA is extracted with a QIAGEN MagAttract™ kit using THERMO FISHER KingFisher™ magnetic particle processors and the supplier's recommended protocols. Integrated transgene copy number analysis is performed using specific Hydrolysis Probe assays for the AAD-1 and Cry34 genes. In addition, contamination by inadvertent integration of the binary vector plasmid backbone is detected by a Hydrolysis Probe assay specific for the Spectinomycin (Spec) resistance gene borne on the binary vector backbone. Hydrolysis Probe assays for endogenous maize genes Invertase; (GenBank™

Accession No. U16123) and Elongation Factor 1α (EF1α) (GENBANK Accession No. AF136823.1) are developed as internal reference standards. Table 4 lists the oligonucleotide sequences of the Hydrolysis Probe assay components (synthesized by INTEGRATED DNA TECHNOLOGIES, Coralville, Iowa).

TABLE 5

Hydrolysis Probe PCR mixture for transgene DNA copy number analysis.

| Reaction Component | μL | Final Concentration |
|---|---|---|
| Water | 0.5 | |
| PVP (10%) | 0.1 | 0.1% |
| ROCHE 2X Master Mix | 5 | 1X |
| Transgene Forward Primer (10 μM) | 0.4 | 0.4 μM |
| Transgene Reverse Primer (10 μM) | 0.4 | 0.4 μM |
| Transgene Probe (5 μM) | 0.4 | 0.2 μM |
| Invertase Forward Primer (10 μM) | 0.4 | 0.4 μM |
| Invertase Reverse Primer (10 μM) | 0.4 | 0.4 μM |
| Invertase Probe (5 μM) | 0.4 | 0.2 μM |

Biplex Hydrolysis Probe PCR reactions are set up according to Table 5 with about 10 ng of DNA, and assay conditions are presented in Table 6.

For amplification, LIGHTCYCLER®480 Probes Master mix (ROCHE APPLIED SCIENCE, Indianapolis, Ind.) is prepared at 1× final concentration in a 10 μL volume multiplex reaction containing 0.1% of PVP, 0.4 μM of each primer, and 0.2 μM of each probe. The FAM (6-Carboxy Fluorescein Amidite) fluorescent moiety is excited at 465 nm and fluorescence is measured at 510 nm; the corresponding values for the HEX (hexachlorofluorescein) fluorescent moiety were 533 nm and 580 nm, and for VIC® the values are 538 nm and 554 nm. The level of fluorescence generated for each reaction is analyzed using the ROCHE LIGHTCYCLER®480 Real-Time PCR system according to the manufacturer's recommendations. Transgene copy number is determined by comparison of LIGHTCYCLER®480 outputs of Target/Reference gene values for unknown samples to Target/Reference gene values of known copy number standards (1-Copy representing hemizygous plants, 2-Copy representing homozygous plants).

TABLE 6

Exemplary Thermocycler conditions for Hydrolysis Probe PCR amplification.

| PCR Steps | Temp (° C.) | Time | No. of cycles |
|---|---|---|---|
| Denature/Activation | 95 | 10 min | 1 |
| Denature | 95 | 10 sec | 40 |
| Anneal/Extend | 58 | 35 sec | |
| Acquire | 72 | 1 sec | |
| Cool | 40 | 10 sec | 1 |

Cp scores, i.e., the point at which the florescence signal crosses the background threshold using the fit points algorithm (LIGHTCYCLER® software release 1.5), and the Relative Quant module (based on the ΔΔCt method), are used to perform the analysis of real time PCR data.

In the LIGHTCYCLER® Fit Points Algorithm software, a graph of the data is made by plotting the logarithm of the input DNA template concentration against the measured Cp values. The slope of the curve is a desired comparison parameter; therefore the initial log input number can be an arbitrary starting point on the curve, with the caveat that the arbitrary concentration values used for input DNA template are representative of the actual serial dilution used. For example, for a 10-fold serial dilution series, the actual inputs concentrations may be 1000, 100, 10 etc., for which points the LC480 Fit Points Algorithm software plots 3, 2, 1 etc. as the logarithms of the inputs. Using a linear regression, the resulting best fit of this line (input log vs Cp) is then used to estimate a slope (m) from an equation of the form y=mx+b. There is an inverse relationship between the starting template amount and Cp value, and therefore the slope (m) is always negative.

A perfect (i.e. 100% efficient) PCR reaction doubles the total template every cycle. PCR efficiency (Eff) is calculated as: Eff=10e(−1/m). Thus, the slope (m) of the graph of log input vs Cp will be −3.3219 for a perfectly efficient reaction (whose efficiency is defined as 2.00). In other words, a 100% efficient PCR reaction is defined by: 2.0=10e(−1/−3.3219). The LC480 Fit Points Algorithm software reports the efficiency value by the first formula. So a 99% efficient reaction has an Eff value of 1.99 rather than 0.99. To express this as a percent efficiency, subtract 1 from this value and multiply by 100 or according to the equation % Eff=[(10e(−1/m)−1)]×100.

Protein analysis of stable transgenic plants: Stable transgenic T0 plants (1 to 2 copies of the transgenes) are transferred to the greenhouse for mature plant production. For each construct, 8 to 12 T0 plants are tested for leaf expression of Cry34 and AAD-1 protein. For T1 analysis, 8-10 plants per event are planted for protein analysis. Data are obtained and compared between constructs with Zm Ubi1 3'UTR and constructs with St PinII 3'UTR. The results show that there is consistent more than 2.5-fold increase in Cry34 protein production using Zm Ubi1 3'UTR (for example pDAB108744) compared to St PinII 3'UTR (for example pDAB108746) in both V4 and V12 leaf stage of the corn plants. Thus, the Zm Ubi1 3'UTR provided is useful in making transgenic traits. In addition, data from ZMEXP9396.1 and ZMEXP9707.1 3'UTR (for example pDAB112396 and pDAB112397) show robust expression of Cry34 protein.

We claim:

1. A nucleic acid construct comprising at least one structural gene of interest functionally linked both to a heterologous promoter and one or more control sequences selected from the group consisting of SEQ ID NOS: 1-3, their full complements, and combinations thereof.

2. The nucleic acid construct of claim 1, wherein the at least one structural gene of interest comprises a gene that confers a non-native phenotype in a plant.

3. The nucleic acid construct of claim 1, wherein the at least one structural gene of interest comprises a gene that confers insect resistance or herbicide resistance/tolerance in a plant.

4. The nucleic acid construct of claim 1, wherein the one or more control sequences are amplified using oligonucleotides selected from the group consisting of SEQ ID NOS: 4-15.

5. The nucleic acid construct of claim 1, wherein the nucleic acid construct comprises a binary vector for *Agrobacterium*-mediated transformation.

6. The nucleic acid construct of claim 1, wherein the nucleic acid construct is stably transformed into a transgenic plant.

7. The nucleic acid construct of claim 6, wherein the transgenic plant is a monocotyledon plant.

8. The nucleic acid construct of claim 6, wherein the transgenic plant is a dicotyledon plant.

9. The nucleic acid construct of claim 1, wherein the nucleic acid construct comprises a selectable marker.

10. The nucleic acid construct of claim 9, wherein the selectable marker comprises an aryloxyalkanoate dioxygenase.

11. The nucleic acid construct of claim 10, wherein the aryloxyalkanoate dioxygenase is AAD-1 or AAD-12.

12. A vector comprising the nucleic acid construct of claim 1.

13. A plant or plant cell transformed with the nucleic acid construct of claim 1.

14. The plant or plant cell of claim 13 further comprising an additional structural gene of interest stacked with the at least one gene of interest.

15. A method for recombinantly producing a peptide or protein comprising functionally linking to a gene encoding the peptide or protein both a heterologous promoter and one or more control sequences selected from the group consisting of SEQ ID NOS: 1-3, their full complements, and combinations thereof.

16. The method of claim 15, wherein the one or more control sequences are amplified using oligonucleotides selected from the group consisting of SEQ ID NOS: 4-15.

17. A method for expression of a gene in a plant or plant cell comprising functionally linking to the gene both a heterologous promoter and one or more control sequences selected from the group consisting of SEQ ID NOS: 1-3, their full complements, and combinations thereof.

18. The method of claim 17, wherein the one or more control sequences are amplified using oligonucleotides selected from the group consisting of SEQ ID NOS: 4-15.

* * * * *

SEQUENCE LISTING

<160> NUMBER OF SEQ ID NOS: 27

<210> SEQ ID NO 1
<211> LENGTH: 910
<212> TYPE: DNA
<213> ORGANISM: Zea mays

<400> SEQUENCE: 1
gtcatgggtc gtttaagctg ccgatgtgcc tgcgtcgtct ggtgccctct ctccatatgg    60

```
aggttgtcaa agtatctgct gttcgtgtca tgagtcgtgt cagtgttggt ttaataatgg      120
accggttgtg ttgtgtgtgc gtactaccca gaactatgac aaatcatgaa taagtttgat      180
gtttgaaatt aaagcctgtg ctcattatgt tctgtctttc agttgtctcc taatatttgc      240
ctgcaggtac tggctatcta ccgtttctta cttaggaggt gtttgaatgc actaaaacta      300
atagttagtg gctaaaatta gttaaaacat ccaaacacca tagctaatag ttgaactatt      360
agctattttt ggaaaattag ttaatagtga ggtagttatt tgttagctag ctaattcaac      420
taacaatttt tagccaacta acaattagtt tcagtgcatt caaacacccc cttaatgtta      480
acgtggttct atctaccgtc tcctaatata tggttgattg ttcggtttgt tgctatgcta      540
ttgggttctg attgctgcta gttcttgctg aatccagaag ttctcgtagt atagctcaga      600
ttcatattat ttatttgagt gataagtgat ccaggttatt actatgttag ctaggttttt      660
tttacaagga taaattatct gtgatcataa ttcttatgaa agctttatgt ttcctggagg      720
cagtggcatg caatgcatga cagcaacttg atcacaccag ctgaggtaga tacggtaaca      780
aggttcttaa atctgttcac caaatcattg gagaacacac atacacattc ttgccagtct      840
tggttagaga aatttcatga caaaatgcca aagctgtctt gactcttcac ttttggccat      900
gagtcgtgac                                                             910

<210> SEQ ID NO 2
<211> LENGTH: 1037
<212> TYPE: DNA
<213> ORGANISM: Zea mays

<400> SEQUENCE: 2
agttctagca gcttgcctgc atgttccgct gtcactgcct cactaggcac gttcacaata       60
ccatcgatgg cttgcctgcc tctatagaat gctgatctac tcttcactgg aggccccctt      120
atatatagga caaaaatccc aattttgttt ggaaaaccac aagtagggat atatctgtcg      180
aattctcgta tgcaacggca acgccgttct acccctcaac tttttttttt cctttttcta      240
ctttgcaaca tgcaacaagg gctgtcattg atcgaaattc aaatatatgt tacattggga      300
attccatgcg actgcctaaa ctctaggaag tttcacttgt cctgtttcat atgtatgtat      360
gcattgtagc cttgttgtat ttcctcaatg tcttggttgc tttcatcggt tagagttctt      420
gacgactgtt gcagagattc tgtcggagta tattcagggt cgcctattac cagacatgct      480
gcccggacaa catgttgatt cgttcattgg cagcgcaaca tgcaattaga aattaacagc      540
tactctagaa caagcaaata acagctgtcg ctaaaattca atattccatc cctgttaaca      600
ttgaatttat tgtcttgttt atgaacccta tgtatctgac agcaccattg ccttttttt       660 acttaggcgg tccattattg tcacacccgg atttaaagag aaagtggat gcatcttata      720 catgcgacaa agaagaaaac atatatatgt atagagataa atgtcataat aacatcaaaa      780
tacttattac aatgcgtaag tcttacaaaa taaaagataa atataaatca aactaaaatc      840
tatctttggc gccaataagt caactgggag atgccaccta gatcagatca aattcctcgt      900
tgtgtggctc ctcttgaacc atctgttctt ctcctgtggg gagtgtgaga cagcaagggt      960
gagctcacac atgttcattg ttcaacaagt tgtggggaat aggagttcat gcgatttgta     1020
aggctaatca acaatag                                                    1037

<210> SEQ ID NO 3
<211> LENGTH: 1061
<212> TYPE: DNA
```

<213> ORGANISM: Zea mays

<400> SEQUENCE: 3

```
gctcagcttc tccatttgca tggtctagta gcttgctttg tactgctagc gccggtcgat      60
ccgtcgcaat cgtcatggat catctctcta tcttgttgtt gcgctgttca taatttggta     120
tatttgccat tccgctattg tgtactcttt ggcatacata caataattaa aatggcgttg     180
cgtggctctc atataattaa ccttcacata acctgaagac tcaagtacgt atagtatggg     240
caactttatt gtagatacta tctggagtct cgaatatttg tcgtccgcta gttcatattt     300
aaactaaaca acgataaata aaaagaact aagtgagtat attttttttgt gggagaaggg     360
ttatccatta atacatccac ggttctgtaa attccatttc atgacatgaa aaaggaaaa     420
acgcatccaa tagcccatta tgtaaatatg tctaccgtct atccattgga caagttatat     480
attaatgact agtttggtaa cctcattttt ttaaggattt tcgttttta agcgaaatta     540
gttcattta ccttggcaaa tagaaatttt ttagaaaaaa atggtgttct caaactagcc     600
ttaaattttt ttagaaatga gaatattatt aatattccat cttccagggg cggatttggg     660
cctcgggcca cctgggccgt ggcccagggc gcagcccaaa aaccctctta tatataggtc     720
ttttttcaac caaaaaatct agaccaaaat acatttcagc ctaaaagatc tcctgctgca     780
ccgattgagt ctggtggcgc tggcggcctc cctcagtcgc tcaagccacg agaacacact     840
cttcaatta tttcgcaaac atgcgcagct gcgtttccta tgttgccagc ggcgcggccg     900
cctccattca gtcctctatc gctctccacg ccttcaggct ctacgaatcc gataagggaa     960
caaggcagca acctctaagg cagccgggcg ggctctgact caggcatccg ccaccgccag    1020
tccgcctcca acgtccctgc gaacctgtag caatgacgcg t                        1061
```

<210> SEQ ID NO 4
<211> LENGTH: 22
<212> TYPE: DNA
<213> ORGANISM: Artificial Sequence
<220> FEATURE:
<223> OTHER INFORMATION: Primer Sequence ASP/ZM Ubi1-3'UTR/1-910

<400> SEQUENCE: 4

```
gtcacgactc atggccaaaa gt                                              22
```

<210> SEQ ID NO 5
<211> LENGTH: 22
<212> TYPE: DNA
<213> ORGANISM: Artificial Sequence
<220> FEATURE:
<223> OTHER INFORMATION: Primer Sequence SP/ZM Ubi1-3'UTR/1-910

<400> SEQUENCE: 5

```
gtcatgggtc gtttaagctg cc                                              22
```

<210> SEQ ID NO 6
<211> LENGTH: 45
<212> TYPE: DNA
<213> ORGANISM: Artificial Sequence
<220> FEATURE:
<223> OTHER INFORMATION: Primer Sequence 3'ZM-Ubi1-3'UTR v1-seamless

<400> SEQUENCE: 6

```
tagcttaatc acctagagct cgtcatgggt cgtttaagct gccga                     45
```

<210> SEQ ID NO 7
<211> LENGTH: 39

```
<212> TYPE: DNA
<213> ORGANISM: Artificial Sequence
<220> FEATURE:
<223> OTHER INFORMATION: Primer Sequence 5'ZM-Ubi1-3'UTR v1-seamless

<400> SEQUENCE: 7
aagctgggtc tagatgtcac gactcatggc caaaagtga                                 39

<210> SEQ ID NO 8
<211> LENGTH: 23
<212> TYPE: DNA
<213> ORGANISM: Artificial Sequence
<220> FEATURE:
<223> OTHER INFORMATION: Primer Sequence 5'ZM-Ubi1-3'UTR v1-seamless

<400> SEQUENCE: 8
agttctagca gcttgcctgc atg                                                  23

<210> SEQ ID NO 9
<211> LENGTH: 27
<212> TYPE: DNA
<213> ORGANISM: Artificial Sequence
<220> FEATURE:
<223> OTHER INFORMATION: Primer Sequence ZMEXP9396.1R

<400> SEQUENCE: 9
ctattgttga ttagccttac aaatcgc                                              27

<210> SEQ ID NO 10
<211> LENGTH: 42
<212> TYPE: DNA
<213> ORGANISM: Artificial Sequence
<220> FEATURE:
<223> OTHER INFORMATION: Primer Sequence ZMEXP9396.1F-seamless

<400> SEQUENCE: 10
tagcttaatc acctagagct cagttctagc agcttgcctg ca                             42

<210> SEQ ID NO 11
<211> LENGTH: 36
<212> TYPE: DNA
<213> ORGANISM: Artificial Sequence
<220> FEATURE:
<223> OTHER INFORMATION: Primer Sequence ZMEXP9396.1R-seamless

<400> SEQUENCE: 11
aagctgggtc tagatctatt gttgattagc cttaca                                    36

<210> SEQ ID NO 12
<211> LENGTH: 25
<212> TYPE: DNA
<213> ORGANISM: Artificial Sequence
<220> FEATURE:
<223> OTHER INFORMATION: Primer Sequence ZMEXP9707.1F

<400> SEQUENCE: 12
gctcagcttc tccatttgca tggtc                                                25

<210> SEQ ID NO 13
<211> LENGTH: 24
<212> TYPE: DNA
<213> ORGANISM: Artificial Sequence
<220> FEATURE:
<223> OTHER INFORMATION: Primer Sequence ZMEXP9707.1R

<400> SEQUENCE: 13
```
acgcgtcatt gctacaggtt cgca                                                  24

<210> SEQ ID NO 14
<211> LENGTH: 42
<212> TYPE: DNA
<213> ORGANISM: Artificial Sequence
<220> FEATURE:
<223> OTHER INFORMATION: Primer Sequence ZMEXP9707.1F-seamless

<400> SEQUENCE: 14
tagcttaatc acctagagct cgctcagctt ctccatttgc at                              42

<210> SEQ ID NO 15
<211> LENGTH: 36
<212> TYPE: DNA
<213> ORGANISM: Artificial Sequence
<220> FEATURE:
<223> OTHER INFORMATION: Primer Sequence ZMEXP9707.1R-seamless

<400> SEQUENCE: 15
aagctgggtc tagatacgcg tcattgctac aggttc                                     36

<210> SEQ ID NO 16
<211> LENGTH: 20
<212> TYPE: DNA
<213> ORGANISM: Artificial Sequence
<220> FEATURE:
<223> OTHER INFORMATION: Primer Sequence AAD1F

<400> SEQUENCE: 16
tgttcggttc cctctaccaa                                                       20

<210> SEQ ID NO 17
<211> LENGTH: 22
<212> TYPE: DNA
<213> ORGANISM: Artificial Sequence
<220> FEATURE:
<223> OTHER INFORMATION: Primer Sequence AAD1R

<400> SEQUENCE: 17
caacatccat caccttgact ga                                                    22

<210> SEQ ID NO 18
<211> LENGTH: 24
<212> TYPE: DNA
<213> ORGANISM: Artificial Sequence
<220> FEATURE:
<223> OTHER INFORMATION: Primer Sequence AAD1P

<400> SEQUENCE: 18
cacagaaccg tcgcttcagc aaca                                                  24

<210> SEQ ID NO 19
<211> LENGTH: 17
<212> TYPE: DNA
<213> ORGANISM: Artificial Sequence
<220> FEATURE:
<223> OTHER INFORMATION: Primer Sequence TQ.8v6.1.F

<400> SEQUENCE: 19
gccataccct ccagttg                                                          17

<210> SEQ ID NO 20
<211> LENGTH: 18
<212> TYPE: DNA
<213> ORGANISM: Artificial Sequence

```
<220> FEATURE:
<223> OTHER INFORMATION: Primer Sequence TQ.8v6.1

<400> SEQUENCE: 20
ccgaatccaa cggcttca                                               18

<210> SEQ ID NO 21
<211> LENGTH: 23
<212> TYPE: DNA
<213> ORGANISM: Artificial Sequence
<220> FEATURE:
<223> OTHER INFORMATION: Primer Sequence TQ.8v6.1.R

<400> SEQUENCE: 21
gccgttgatg gagtagtaga tgg                                         23

<210> SEQ ID NO 22
<211> LENGTH: 19
<212> TYPE: DNA
<213> ORGANISM: Artificial Sequence
<220> FEATURE:
<223> OTHER INFORMATION: Primer Sequence SPC1A

<400> SEQUENCE: 22
cttagctgga taacgccac                                              19

<210> SEQ ID NO 23
<211> LENGTH: 19
<212> TYPE: DNA
<213> ORGANISM: Artificial Sequence
<220> FEATURE:
<223> OTHER INFORMATION: Primer Sequence SPC1S

<400> SEQUENCE: 23
gaccgtaagg cttgatgaa                                              19

<210> SEQ ID NO 24
<211> LENGTH: 21
<212> TYPE: DNA
<213> ORGANISM: Artificial Sequence
<220> FEATURE:
<223> OTHER INFORMATION: Primer Sequence TQSPC

<400> SEQUENCE: 24
cgagattctc cgcgctgtag a                                           21

<210> SEQ ID NO 25
<211> LENGTH: 18
<212> TYPE: DNA
<213> ORGANISM: Artificial Sequence
<220> FEATURE:
<223> OTHER INFORMATION: Primer Sequence InvertaseF

<400> SEQUENCE: 25
tggcggacga cgacttgt                                               18

<210> SEQ ID NO 26
<211> LENGTH: 19
<212> TYPE: DNA
<213> ORGANISM: Artificial Sequence
<220> FEATURE:
<223> OTHER INFORMATION: Primer Sequence InvertaseR

<400> SEQUENCE: 26
aaagtttgga ggctgccgt                                              19
```

```
<210> SEQ ID NO 27
<211> LENGTH: 21
<212> TYPE: DNA
<213> ORGANISM: Artificial Sequence
<220> FEATURE:
<223> OTHER INFORMATION: Primer Sequence InvertaseP

<400> SEQUENCE: 27
cgagcagacc gccgtgtact t                                              21
```